(12) United States Patent
Hirai et al.

(10) Patent No.: US 9,115,391 B2
(45) Date of Patent: Aug. 25, 2015

(54) METHOD OF DETECTING A POLYMORPHISM AT A POLYMORPHISM SITE

(75) Inventors: Mitsuharu Hirai, Kyoto (JP); Toshiya Hosomi, Kyoto (JP); Aki Iguchi, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 1209 days.

(21) Appl. No.: 13/002,194

(22) PCT Filed: Jul. 2, 2009

(86) PCT No.: PCT/JP2009/062143
§ 371 (c)(1),
(2), (4) Date: Feb. 1, 2011

(87) PCT Pub. No.: WO2010/001969
PCT Pub. Date: Jan. 7, 2010

(65) Prior Publication Data
US 2011/0117568 A1    May 19, 2011

(30) Foreign Application Priority Data
Jul. 2, 2008    (JP) .................................. 2008-173986

(51) Int. Cl.
*C12Q 1/68* (2006.01)
*C12P 19/34* (2006.01)

(52) U.S. Cl.
CPC ............ *C12Q 1/6827* (2013.01); *C12Q 1/6858* (2013.01)

(58) Field of Classification Search
USPC ............................... 435/6.12, 91.2; 536/24.33
See application file for complete search history.

(56) References Cited

U.S. PATENT DOCUMENTS

| | | | |
|---|---|---|---|
| 4,889,818 A | 12/1989 | Gelfand et al. | ............... 435/194 |
| 5,079,352 A | 1/1992 | Gelfand et al. | ............... 536/23.2 |

(Continued)

FOREIGN PATENT DOCUMENTS

| | | | |
|---|---|---|---|
| EP | 0332435 | 9/1989 | ............... C12Q 1/68 |
| EP | 0455430 | 11/1991 | ............... C12N 9/12 |

(Continued)

OTHER PUBLICATIONS

Office Action issued in corresponding European Patent Application No. 09773547.6 dated Nov. 7, 2013.

(Continued)

*Primary Examiner* — Kenneth Horlick
(74) *Attorney, Agent, or Firm* — Morgan, Lewis & Bockius LLP

(57) ABSTRACT

The present invention provides a method for detecting a mutation capable of detecting a mutation with high sensitivity and high reliability in one reaction system. Using primers (Xmt) and (Xwt), a target nucleic acid sequence whose objective base to be detected is a mutant-type is amplified with amplification efficiency higher than a target nucleic acid sequence whose objective base to be detected is a normal-type. The (Xmt) is a primer that is complementary to a region including a mutant-type base in the template nucleic acid and has a base complementary to a mutant-type base at a 3' region, and the (Xwt) is a primer that is complementary to a region including a normal-type base in the template nucleic acid and has a base complementary to a normal-type base at a 3' region. It is preferable that amplification efficiency by the (Xmt) with reference to a mutant-type template nucleic acid is higher than that by the (Xwt) with reference to a normal-type template nucleic acid. Then, a signal value that shows a molten state of a hybridization product between the thus obtained amplification product and the probe is measured, and the presence or absence of the mutation of the objective base site is determined from a change in the signal value accompanying a change in the temperature.

18 Claims, 6 Drawing Sheets

(56) References Cited

U.S. PATENT DOCUMENTS

| | | | |
|---|---|---|---|
| 5,972,602 A * | 10/1999 | Hyland et al. | 435/6.11 |
| 6,472,156 B1 * | 10/2002 | Wittwer et al. | 435/6.1 |
| 2003/0224434 A1 * | 12/2003 | Wittwer et al. | 435/6 |
| 2007/0154892 A1 | 7/2007 | Wain-Hobson et al. | |
| 2007/0184457 A1 | 8/2007 | Pont-Kingdon et al. | |
| 2008/0044812 A1 | 2/2008 | Molloy et al. | |
| 2009/0104616 A1 | 4/2009 | Hosomi | 435/6 |
| 2009/0208954 A1 | 8/2009 | Hirai et al. | 435/6 |
| 2009/0208956 A1 | 8/2009 | Hirai et al. | 435/6 |
| 2009/0269756 A1 | 10/2009 | Majima et al. | 435/6 |
| 2010/0112559 A1 | 5/2010 | Hirai et al. | 435/6 |
| 2010/0297617 A1 | 11/2010 | Hirai et al. | 435/6 |
| 2011/0117568 A1 | 5/2011 | Hirai et al. | |

FOREIGN PATENT DOCUMENTS

| | | | |
|---|---|---|---|
| EP | 1619258 A1 | 1/2006 | |
| EP | 1686190 A1 | 8/2006 | |
| EP | 2025764 A1 | 2/2009 | |
| EP | 2314680 A1 | 4/2011 | |
| JP | 2853864 | 2/1990 | C12Q 1/68 |
| JP | 2004-337124 | 2/2004 | C12N 15/09 |
| JP | 2004-337124 A | 12/2004 | |
| JP | 2006-230401 A | 9/2006 | |
| WO | WO 91/09950 | 7/1991 | C12N 15/54 |
| WO | WO 92/09689 | 6/1992 | C12N 15/00 |
| WO | 2006/133184 A2 | 12/2006 | |
| WO | WO 2008066136 | 6/2008 | C12N 15/00 |
| WO | WO 2008066161 | 6/2008 | C12N 15/00 |
| WO | WO 2008066162 | 6/2008 | C12Q 1/68 |
| WO | WO 2008066163 | 6/2008 | C12N 15/09 |
| WO | WO 2008066164 | 6/2008 | C12N 15/09 |
| WO | WO 2008066165 | 6/2008 | C12N 15/00 |
| WO | 2010/001969 A1 | 1/2010 | |

OTHER PUBLICATIONS

Extended European Search Report issued in related European Patent Application No. 11734760.9 dated Jan. 8, 2014.

Wang et al., "High-throughput SNP genotyping by single-tube PCR with Tm-shift primers," BioTechniques, 39: 885-893 (2005).

Casado-Diaz et al., "Indvidual single tube genotyping and DNA pooling by allele-specifc PCR to uncover associations of polymorphisms with complex diseases" Clinica Chimica Acta, 2007, vol. 376, pp. 155-162.

Extended European Search Report of the corresponding European Application No. 09773547.6 dated Nov. 14, 2011.

Germer at al., "Single-Tube Genotyping without Oligonucleotide Probes" Genome Res., 1999, vol. 9, No. 1, pp. 72-78.

Rust et al., "Mutagenically separated PCR (MS-PCR): a highly specific one step procedure for easy mutation detection" Nucleic Acids Research, 1993, vol. 21, No. 16, pp. 3623-3629.

Senescau et al., "Use of a Locked-Nucleic-Acid Oligomer in the Clamped Probe Assay for Detection of a Minority Pfcrt K76T Mutant Population of Plasmodium falciparum" Journal of Clinical Microbiology, 2005, vol. 43, No. 7, pp. 3304-3308.

Office Action issued in corresponding Chinese Patent Application No. 200980125546.7 dated Feb. 29, 2012.

Zhou, Chenhui et al., "Application of a Bidirectional Amplification of Specific Alleles Polymerase Chain Reaction Technique in Study of SNPs," Journal of Chongqing Medical University, 31: 658-661 (2006), English Abstract only.

Crockett et al., "Fluorescein-Labeled Oligonucleotides for Real-Time PCR: Using the Inherent Quenching of Deoxyguanosine Nucleotides", Analytical Biochemistry 290(1): 89-97 (2001).

International Search Report for PCT JP/2009/062143 (mailed Aug. 25, 2009).

Office Action issued in related U.S. Appl. No. 13/388,272 dated Jun. 6, 2014.

Office Action issued in related U.S. Appl. No. 13/388,272 dated Nov. 24, 2014.

Kwok et al., "Detection of Single Nucleotide Polymorphisms," Current Issues in Molecular Biology, 5: 43-60 (2003).

* cited by examiner

METHOD OF DETECTING A POLYMORPHISM AT A POLYMORPHISM SITE

RELATED APPLICATIONS

The present application is a 371 filing based on PCT/JP2009/062143, filed Jul. 2, 2009, which claims priority to Japanese Application No. 2008-173986, filed Jul. 2, 2008, all of which are here by incorporated by reference in their entireties.

SEQUENCE LISTING SUBMISSION VIA EFS-WEB

A computer readable text file, entitled "68022-5043-SequenceListing.txt," created on or about Dec. 30, 2010 with a file size of about 3 kb contains the sequence listing for this application and is hereby incorporated by reference in its entirety.

TECHNICAL FIELD

The present invention relates to a method for amplifying a target nucleic acid sequence including a base site where an objective mutation to be detected occurs, a method for detecting a mutation using the same, and a reagent used for the same.

BACKGROUND ART

Detection of mutations of genes including a single nucleotide polymorphism (SNP) is widely conducted in prevention and treatment for all sorts of diseases. For example, many mutations are observed in genes of cancer cells and it is known that these mutations are involved in malignant transformation of cells. Therefore, detection of mutations of genes in cells makes it possible to detect stage progression of malignant transformation, and it is considered as very useful tool in treatment. Further, it is reported that there are mutations showing drug resistance in genes of cancer cells on medication. Since detection of these mutations makes it possible to judge effectiveness of drugs for each patient, further appropriate treatment can be conducted. For example, although a treatment with medication of an anticancer agent "imatinib" is widely conducted for chronic myelogenous leukemia (CML), it is considered that a mutation (for example, T315I) of the bcr-abl gene affects drug resistance. Since detection of mutations of genes is useful for early detection and treatment in a clinical field, high reliability of the detection is required.

As the method for detecting mutations of genes, a direct sequencing method, an ASP (allele specific primer)-PCR (polymerase chain reaction) method (Patent Document 1), and a Tm (melting temperature) analysis method (Non Patent Document 1) are generally known. The direct sequencing method is a method in which a region including an objective base site to be detected is amplified and a base sequence of the thus obtained amplification product is analyzed. The ASP-PCR method is a method in which PCR is conducted using a primer that is complementary to a region including an objective base site to be detected and has a base complementary to a base of the objective base site to be detected at the 3' end region and a mutation is judged on the presence or absence of amplification. According to this method, for example, when a primer that is complementary to a sequence in which the objective base site to be detected is set as a mutant-type base (hereinafter, also referred to as a "mutant sequence") is used, a mutation can be checked by the detection of the amplification. Further, when a primer that is complementary to a sequence in which the objective base site to be detected is set as a normal-type base (hereinafter, also referred to as a "normal sequence") is used, a non-mutation (i.e., normal) can be checked by the detection of the amplification. In the Tm analysis, first, a region including the objective base site to be detected is amplified and a hybrid (double-stranded DNA) between the thus obtained amplification product and a probe that is complementary to the mutant sequence is formed. Then, this hybridization product is heat-treated, dissociation (melting) of the hybrid accompanying the temperature rise is detected by measuring signals such as an absorbance and the like, and thus a Tm value is determined. Accordingly, the presence or absence of the mutation is judged. The more the respective chains of the hybridization product match, the higher the Tm value, and the less the respective chains of the hybridization product match, the lower the Tm value. Therefore, when the Tm value (reference value for assessment) is determined beforehand with respect to the hybridization product between the mutant sequence and a probe that is complementary thereto, and this reference value is compared to the determined Tm value (measurement value), the following judgment can be made. When the measurement value is identical to the reference value, it is considered as perfect match, that is, it can be judged that a mutation is present in the objective base site to be detected. On the other hand, when the measurement value is lower than the reference value, it is considered as mismatching, that is, it can be judged that the objective base site to be detected is normal, i.e., no mutation is present.

However, the direct sequencing method has low sensitivity and the operation thereof requires considerable time and effort. The ASP-PCR method has high sensitivity, but has low specificity. That is, when a primer that is complementary to the mutant sequence is used, there is a possibility that amplification is observed even though no mutation is present and that it is judged as false-positive. Further, in the ASP-PCR method, only one of a primer that is complementary to the mutant sequence and a primer that is complementary to the normal sequence can be used in one reaction system. Therefore, in order to check whether the objective base site to be detected is normal or mutant, PCR should be conducted with reference to two reaction systems that is a reaction system using a primer that is complementary to the mutant sequence and a reaction system using a primer that is complementary to the normal sequence. Since the ASP-PCR method uses two reaction systems, the operation thereof requires time and effort and it is costly. Further, there is a problem that the judgment with sufficient reliability is difficult even though two reaction systems are used. That is, with respect to the two reaction systems, when no amplification is observed in the reaction system using a primer that is complementary to the normal sequence and the amplification is observed in the reaction system using a primer that is complementary to the mutant sequence, it can be judged as positive with no doubt. However, when the amplification is observed in the both reaction systems, it is still difficult to judge whether the objective base site to be detected is normal or mutant. On the other hand, since the Tm analysis method has high specificity, the problem of a false-positive can be avoided. Further, it can be judged whether the objective base site to be detected is normal or mutant in one reaction system. However, there is a problem that the Tm analysis method has insufficient sensitivity.

Particularly, when a mutation relating to a cancer is detected as described above, both cells in which objective genes are mutated and cells in which objective genes are normal are present in specimens collected from patients. Therefore, it is required to detect the presence or absence of the mutation accurately with respect to, for example, biological samples containing large amounts of normal genes and small amounts of mutant genes.

Patent Document 1: JP 2853864 B

Non Patent Document 1: Analytical Biochemistry 290, 89-97 (2001)

DISCLOSURE OF INVENTION

Problem to be Solved by the Invention

Hence, the present invention is intended to provide a method for amplifying a target nucleic acid sequence that achieves detection of mutation with high sensitivity and high reliability easily in one reaction system, a method for detecting the mutation, and a reagent used for the same.

Means for Solving Problem

In order to achieve the aforementioned object, the method of the present invention for amplifying a target nucleic acid sequence is a method for amplifying a target nucleic acid sequence in a template nucleic acid, wherein the target nucleic acid sequence is a sequence including a base site where an objective mutation to be detected occurs in the template nucleic acid, and the method includes an amplification step for amplifying a target nucleic acid sequence whose base site is a mutant-type base preferentially over a target nucleic acid sequence whose base site is a normal-type base in the same reaction system.

The method of the present invention for detecting a mutation is a method for detecting the presence or absence of a mutation of an objective base site to be detected in a template nucleic acid, including steps of:
(a) amplifying a target nucleic acid sequence including the base site in the template nucleic acid by the method of the present invention for amplifying a target nucleic acid sequence in a reaction system;
(b) changing a temperature of the reaction system containing an amplification product obtained in the step (a) in the presence of a probe capable of hybridizing to a sequence including the base site in the template nucleic acid, and measuring a signal value that shows a molten state of a hybridization product between the amplification product and the probe; and
(c) determining the presence or absence of the mutation of the objective base site from a change in the signal value accompanying a change in the temperature.

Effects of the Invention

In the present invention, for example, even in a case where a template nucleic acid whose base site is a mutant-type and a template nucleic acid whose base site is a normal-type are present in a sample as template nucleic acids, the mutant-type target nucleic acid sequence is amplified preferentially over the normal-type target nucleic acid sequence. In this manner, by preferentially amplifying the mutant-type target nucleic acid sequence, for example, even in a case where the proportion of the mutant-type template nucleic acid is lower than that of the normal-type template nucleic acid, the presence or absence of the mutation can be detected with high sensitivity and high reliability by conducting the Tm analysis using a probe of the present invention with reference to the amplification product. Therefore, as described above, it is particularly useful for samples containing both normal genes and mutant genes. From these points, it can be said that the present invention is very useful, for example, in a clinical field in which treatment and diagnosis are conducted by detecting mutations of genes.

DESCRIPTION OF THE INVENTION

Figure 1:
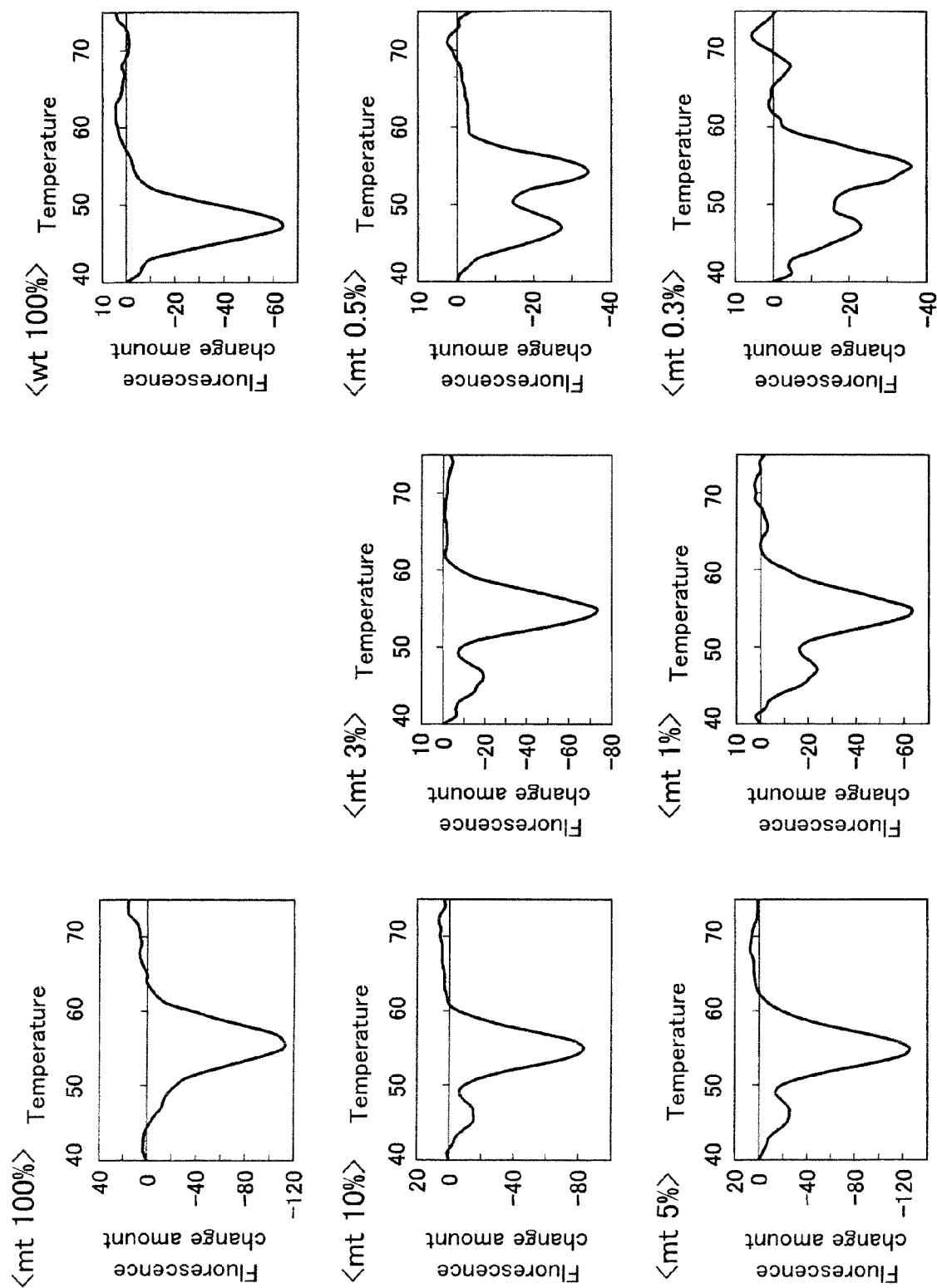
FIG. 1 includes graphs showing the results of Tm analysis in Example 1 of the present invention.

<Method for Amplifying Target Nucleic Acid Sequence>

As described above, the method of the present invention for amplifying a target nucleic acid sequence is a method for amplifying a target nucleic acid sequence in a template nucleic acid, wherein the target nucleic acid sequence is a sequence including a base site where an objective mutation to be detected occurs in the template nucleic acid, and the method includes an amplification step for amplifying a target nucleic acid sequence whose base site is a mutant-type base preferentially over a target nucleic acid sequence whose base site is a normal-type base in the same reaction system.

In the present invention, hereinafter, a template nucleic acid whose base site is a mutant-type base is also referred to as a "mutant-type template nucleic acid", a target nucleic acid sequence whose base site is a mutant-type base is also referred to as a "mutant-type target nucleic acid sequence", a template nucleic acid whose base site is a normal-type base is also referred to as a "normal-type template nucleic acid", and a target nucleic acid sequence whose base site is a normal-type base is also referred to as a "normal-type target nucleic acid sequence". In the method of the present invention for amplifying a target nucleic acid sequence, for example, a normal-type template nucleic acid can be amplified when the template nucleic acid only includes a normal-type template nucleic acid, a mutant-type template nucleic acid can be amplified when the template nucleic acid only includes a mutant-type template nucleic acid, and both a normal-type template nucleic acid and a mutant-type template nucleic acid can be amplified when the template nucleic acid includes both the normal-type template nucleic acid and the mutant-type template nucleic acid.

In the present invention, "preferentially amplifying a mutant-type target nucleic acid sequence" may mean, for example, that amplification of a mutant-type target nucleic acid sequence is promoted or that amplification of a normal-type target nucleic acid sequence is suppressed or inhibited.

In the present invention, for example, amplification may be performed using a single-stranded nucleic acid as a template nucleic acid. Alternatively, with reference to a complementary double-stranded nucleic acid, amplification may be performed using two single-stranded nucleic acids of the complementary double-stranded nucleic acid as templates, respectively. In the present invention, when two single-stranded nucleic acids of the double-stranded nucleic acid are respectively used as templates, for convenience sake, one of the single-stranded nucleic acids is also referred to as a (+) strand and the other of the single-stranded nucleic acids is also referred to as a (−) strand. It is to be noted that, in the present invention, either one of the (+) strand or the (−) strand can be a sense strand or an antisense strand. Further, in the method of the present invention for detecting a mutation that will be described later, an objective base site to be detected may be, for example, a base site of a (+) strand or a base site of a (−) strand corresponding to the base site. A probe of the present invention used in the method for detecting a mutation that will be described later can be designed, for example, so as to be capable of hybridizing to the (+) strand or hybridizing to the (−) strand.

According to the method of the present invention for amplifying a target nucleic acid sequence, as described above, a mutant-type target nucleic acid sequence can be amplified preferentially over a normal-type target nucleic acid sequence. Therefore, the method of the present invention for amplifying a target nucleic acid sequence can be regarded as a method for amplifying a mutant-type target nucleic acid sequence, for example. The method of the present invention for amplifying a target nucleic acid sequence is applicable as long as a mutant-type target nucleic acid sequence can be amplified preferentially over a normal-type target nucleic acid sequence, and other steps and conditions are not limited at all. Specific examples of the present invention are described below. However, the present invention is not limited thereto.

First Embodiment

As the first method of the present invention for amplifying a target nucleic acid sequence, for example, the first amplification reagent containing a primer (Xmt) and a primer (Xwt) is used. Specifically, the amplification step is a step for amplifying the target nucleic acid sequence using the primer (Xmt) and the primer (Xwt) in the same reaction system.
Primer (Xmt)
Primer that is complementary to a region including a mutant-type base site in the template nucleic acid and has a base complementary to a base of the base site at a 3' region
Primer (Xwt)
Primer that is complementary to a region including a normal-type base site in the template nucleic acid and has a base complementary to a base of the base site at a 3' region In the present invention, hereinafter, a region in the template nucleic acid to which respective primers are annealed is also referred to as an "annealing region". Further, in the present invention, respective primers are applicable as long as they can be bound specifically to an annealing region in the template nucleic acid. The primer may be a sequence that is perfectly complementary to the annealing region, a sequence that is partially complementary to the annealing region, or a sequence including a base partially mismatching the annealing region. The same applies to other embodiments.

Figure 6:
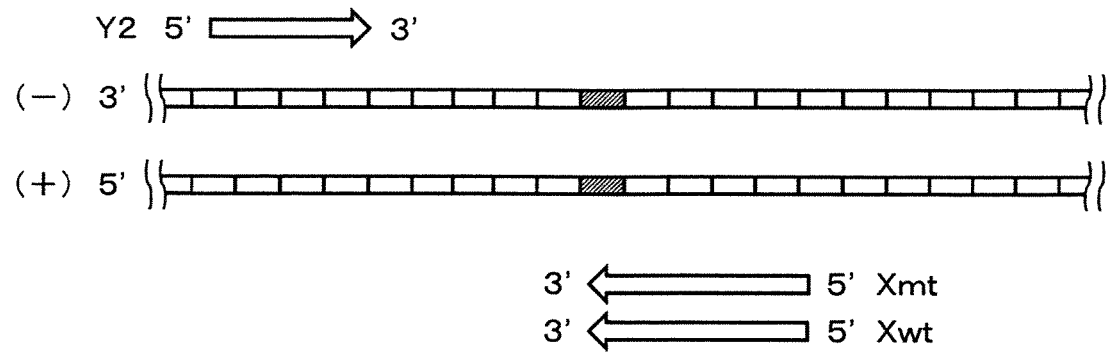
FIG. 6 is a schematic showing the relationship between a primer and a template nucleic acid in an embodiment of the present invention.

The primer (Xmt) is a primer that can anneal to a region whose base site is a mutant-type, and, hereinafter, is also referred to as a "mutant-type primer". On the other hand, the primer (Xwt) is a primer that can anneal to a region whose base site is a normal-type, and, hereinafter, is also referred to as a "normal-type primer". As described above, the template nucleic acid may be a single-stranded nucleic acid or a double-stranded nucleic acid. When the template nucleic acid is a double-stranded nucleic acid, for example, it is preferable to design the mutant-type primer (Xmt) and the normal-type primer (Xwt) so as to be complementary to either one of the single-stranded nucleic acids of the double-stranded nucleic acid. Further, for example, it is preferable to design the primer (Y2) that will be described later so as to be complementary to the other of the single-stranded nucleic acids. A schematic of FIG. 6 shows an example of the relationship between a template nucleic acid and a primer. In FIG. 6, (+) and (−) each indicate a single-stranded nucleic acid of a double-stranded template nucleic acid, and the shaded areas indicate the objective base sites to be detected. As shown in FIG. 6, the mutant-type primer (Xmt) and the normal-type primer (Xwt) are both designed as primers that are complementary to the (+) strand. In this case, it is preferable that the primer (Y2) is designed as a primer that is complementary to the (−) strand. It is to be noted that FIG. 6 is a schematic showing a mere example and does not limit, for example, the length of each primer and the annealing region in the template nucleic acid, and the primer (Y2) is also optional. Further, the mutant-type primer (Xmt) and the normal-type primer (Xwt) may both be designed as primers that are complementary to the (−) strand, and the primer (Y2) may be designed as a primer that is complementary to the (+) strand.

In this embodiment, it is preferable that the primer (Xmt) and the primer (Xwt) satisfy the relationship that amplification efficiency by the primer (Xmt) with reference to the template nucleic acid whose base site is a mutant-type is higher than amplification efficiency by the primer (Xwt) with reference to the template nucleic acid whose base site is a normal-type. This allows the following, for example. That is, even when the template nucleic acid includes a normal-type template nucleic acid and a mutant-type template nucleic acid and the content of the mutant-type template nucleic acid is low, since amplification efficiency by the primer (Xmt) with reference to the mutant-type template nucleic acid is higher than that of the primer (Xwt) with reference to the normal-type template nucleic acid, a low content of the mutant-type template nucleic acid can be amplified efficiently. Therefore, even with a low content of the mutant-type template nucleic acid, for example, an amplification product of the degree capable of being detected in the Tm analysis that will be described later can be obtained and thus the mutant-type template nucleic acid can be detected. In the present invention, for example, even when the content of the mutant-type template nucleic acid in the template nucleic acid is about 0.1%, an amplification product capable of being detected in the Tm analysis that will be described later can be obtained.

Further, when the template nucleic acid only includes a mutant-type template nucleic acid or a normal-type template nucleic acid, each can be amplified by the mutant-type primer (Xmt) or the normal-type primer (Xwt). Therefore, as described above, not only in the case where the template nucleic acid includes both the mutant-type template nucleic acid and the normal-type template nucleic acid but also in the case where the template nucleic acid includes either one of the mutant-type template nucleic acid or the normal-type template nucleic acid, it can be detected by the Tm analysis that will be described later. It is to be noted that when the template nucleic acid only includes a normal-type template nucleic acid, for example, there is a possibility that not only the normal-type primer but also the mutant-type primer anneals to the template nucleic acid to elongate. However, in this embodiment, the amplification efficiency of the mutant-type primer (Xmt) with reference to the "mutant-type" template nucleic acid is set higher than that of the normal-type primer (Xwt) with reference to the "normal-type" template nucleic acid. Therefore, the amplification efficiency of the mutant-type primer (Xmt) with reference to the "normal-type" template nucleic acid is lower than that of the normal-type primer (Xwt) with reference to the "normal-type" template nucleic acid, and the normal-type primer shows much higher amplification efficiency with reference to the normal-type template nucleic acid. Therefore, even when amplification by the mutant-type primer occurs mistakenly, in terms of the amplification efficiency, for example, it is difficult to amplify to the degree capable of obtaining sufficient detection sensitivity in the Tm analysis that will be described later. As a result, for example, in the Tm analysis, the problem of a false-positive caused by erroneous amplification can be prevented.

The mutant-type primer (Xmt) and the normal-type primer (Xwt) are not particularly limited and those satisfying the aforementioned relationship can preferably be used. Such a relationship can be achieved by setting an affinity of the mutant-type primer (Xmt) with reference to the mutant-type template nucleic acid, i.e., ease of annealing, higher than that of the normal-type primer (Xwt) with reference to the normal-type template nucleic acid. Further, for example, such a relationship can be achieved by encouraging an elongation reaction of the mutant-type primer (Xmt) annealed to the mutant-type template nucleic acid rather than an elongation reaction of the normal-type primer (Xmt) annealed to the normal-type template nucleic acid.

The method for adjusting an affinity of the primer is not particularly limited and can be conducted, for example, by the setting of the Tm value. In this embodiment, for example, it is preferable that the Tm value of the mutant-type primer (Xmt) with reference to the complementary sequence is relatively higher than that of the normal-type primer (Xwt) with reference to the complementary sequence. Since annealing of the mutant-type primer (Xmt) to the template nucleic acid can be improved over that of the normal-type primer (Xwt) by setting the Tm value of the mutant-type primer (Xmt) higher than that of the normal-type primer (Xwt), amplification efficiency by the mutant-type primer (Xmt) can be improved. The difference between the Tm value of the mutant-type primer (Xmt) and the Tm value of the normal-type primer (Xwt) is not particularly limited, however is, for example, higher than 0° C. and 20° C. or lower, preferably higher than 0° C. and 10° C. or lower, and particularly preferably higher than 0° C. and 5° C. or lower. In this state, the Tm value in the primer design means, for example, the Tm value with reference to a hybridization product between a normal-type primer and a base sequence 100% complementary thereto or the Tm value with reference to a hybridization product between a mutant-type primer and a base sequence 100% complementary thereto.

The method for setting the Tm value of the mutant-type primer (Xmt) and the Tm value of the normal-type primer (Xwt) is not particularly limited and the Tm value can be adjusted, for example, by the length of each primer and the GC content. When the Tm value is adjusted by the length of the primer, generally, the relatively longer the primer is, the relatively higher the Tm value can be set. In this embodiment, for example, it is preferable that the length of the mutant-type primer (Xmt) is set longer than that of the normal-type primer (Xwt). Thereby, the Tm value of the mutant-type primer (Xmt) can be set relatively higher than that of the normal-type primer (Xwt). Further, when the Tm value is adjusted by the GC content, for example, the relatively higher the GC content is, the relatively higher the Tm value can be set. In this embodiment, for example, it is preferable that the GC content of the mutant-type primer (Xmt) is set higher than that of the normal-type primer (Xwt). Further, the Tm value can be set by adjusting both the length of the primer and the GC content. Other than these, for example, by employing sequences including LNA that is an RNA analog, PNA that is a peptide nucleic acid, BNA that is a cross-linking nucleic acid, and the like, for example, the Tm value can be set relatively higher than the sequence that does not include these nucleic acids.

When the length of the mutant-type primer (Xmt) is set longer than that of the normal-type primer (Xwt), the difference therebetween is not particularly limited, however is, for example, more than 0 bases and 20 bases or less, preferably more than 0 bases and 10 bases or less, and more preferably more than 0 bases and 5 bases or less.

Reactivity of an elongation reaction from the primer is adjustable, for example. The method for adjusting is not particularly limited and the adjustment can be conducted by known methods. Specific examples thereof include a method in which substances such as a fluorescent substance, biotin, and the like are added to a 5' region of the mutant-type primer (Xmt), a method in which an additional sequence is added to a 5' region of the mutant-type primer (Xmt), and the like. These methods can be conducted according to the description of JP2004-337124 A.

The mutant-type primer (Xmt) is applicable as long as a base complementary to a base (i.e., mutant-type base) of the objective base site to be detected is present at the 3' region thereof. For example, it is preferable that the first or the second base of the 3' end is a base complementary to the mutant-type base. Specifically, for example, when a sequence of a template nucleic acid is "5'- . . . acGtt . . . -3'" and the mutant-type base is the underlined part "G", the mutant-type primer (Xmt) can be designed as a sequence "5'- . . . aaC-3'" in which the first base of the 3' end is a complementary base (C) of the mutant-type base (G). Further, the mutant-type primer (Xmt) may be designed as a sequence "5'- . . . aaCg-3'" in which the second base of the 3' end is a complementary base (C) of the mutant-type base (G). The first base of the 3' end means the base at the 3' end and the second base of the 3' end means the second base in the direction toward the 5' end with the base at the 3' end being considered as the first base (hereinafter, the same applies).

In the former case, it is preferable that the first base of the 3' end is designed as a base complementary to the mutant-type base and at least one of the bases from the second base of the 3' end to the 5' end is designed as a base (i.e., mismatching base) mismatching to the template nucleic acid. Above all, it is preferable that at least one of the second base and the third base of the 3' end is designed as the mismatching base, and it is more preferable that the second base of the 3' end is designed as the mismatching base. Specifically, for example, when a sequence in a template nucleic acid is "5'- . . . acGtt . . . -3'" and the mutant-type base is the underlined part "G" in the same manner as described above, the mutant-type primer (Xmt) may be designed as a sequence "5'- . . . atC . . . -3'" in which the first base of the 3' end is a complementary base (C) of the mutant-type base (G) and the second base of the 3' end is not a base (a) complementary to a base (t) of the template nucleic acid but a mismatching base (t). Further, in the latter case, it is preferable that the second base of the 3' end is designed as a base complementary to the mutant-type base and at least one of the first base of the 3' end and/or bases from the third base of the 3' end to the 5' end is designed as a base (i.e., mismatching base) mismatching to the template nucleic acid. Above all, it is preferable that at least one of the first base and the third base of the 3' end is designed as the mismatching base, and it is more preferable that the third base of the 3' end is designed as the mismatching base. Specifically, for example, when a sequence in a template nucleic acid is "5'-... acGtt ... -3'" and the mutant-type base is the underlined part "G" in the same manner as described above, the mutant-type primer (Xmt) may be designed as a sequence "5'-... atCg ... -3'" in which the second base of the 3' end is a complementary base (C) of the mutant-type base (G) and the third base of the 3' end is not a base (a) complementary to a base (t) of the template nucleic acid but a mismatching base (t). By adding a mismatching base to a mutant-type primer in this manner, specificity of the mutant-type primer (Xmt) to the mutant-type template nucleic acid can be further improved.

The normal-type primer (Xwt) is applicable as long as a base complementary to a base (i.e., normal-type base) of the objective base site to be detected is present at the 3' region thereof. For example, it is preferable that the first or the second base of the 3' end is a base complementary to the normal-type base. Specifically, for example, when a sequence of a template nucleic acid is "5'-... acAtt ... -3'" and the normal-type base is the underlined part "A", the normal-type primer (Xwt) can be designed as a sequence "5'-... aaT-3'" in which the first base of the 3' end is a complementary base (T) of the normal-type base (A). Further, the normal-type primer (Xwt) may be designed as a sequence "5'-... aaTg-3'" in which the second base of the 3' end is a complementary base (T) of the normal-type base (A).

In the former case, it is preferable that the first base of the 3' end is designed as a base complementary to the normal-type base and at least one of the bases from the second base of the 3' end to the 5' end is designed as a base (i.e., mismatching base) mismatching to the template nucleic acid. Above all, it is preferable that at least one of the second base and the third base of the 3' end is designed as the mismatching base, and it is more preferable that the second base of the 3' end is designed as the mismatching base. Specifically, for example, when a sequence in a template nucleic acid is "5'-... acAtt ... -3'" and the normal-type base is the underlined part "A" in the same manner as described above, the normal-type primer (Xwt) may be designed as a sequence "5'-... atA ... -3'" in which the first base of the 3' end is a complementary base (T) of the mutant-type base (A) and the second base of the 3' end is not a base (a) complementary to a base (t) of the template nucleic acid but a mismatching base (t). Further, in the latter case, it is preferable that the second base of the 3' end is designed as a base complementary to the normal-type base and at least one of the first base of the 3' end and/or bases from the third base of the 3' end to the 5' end is designed as a base (i.e., mismatching base) mismatching to the template nucleic acid. Above all, it is preferable that at least one of the first base and the third base of the 3' end is designed as the mismatching base, and it is more preferable that the third base of the 3' end is designed as the mismatching base. Specifically, for example, when a sequence in a template nucleic acid is "5'-... acAtt ... -3'" and the mutant-type base is the underlined part "A" in the same manner as described above, the normal-type primer (Xwt) may be designed as a sequence "5'-... atAg ... -3" in which the second base of the 3' end is a complementary base (T) of the normal-type base (A) and the third base of the 3' end is not a base (a) complementary to a base (t) of the template nucleic acid but a mismatching base (t). By adding a mismatching base to a normal-type primer in this manner, specificity of the normal-type primer (Xwt) to the normal-type template nucleic acid can be further improved.

The length of the mutant-type primer (Xmt) and the normal-type primer (Xwt) is not particularly limited and, as a common length, is, for example, 10 to 50 bases, preferably 15 to 40 bases, and further preferably 16 to 35 bases.

In the amplification step of the present invention, as described above, it is preferable that the following primer (Y2) is used in combination with the mutant-type primer (Xmt) and the normal-type primer (Xwt).

Primer (Y2)

Primer that is complementary to a complementary sequence for a region at a 5' side relative to the base site in the template nucleic acid The primer (Y2) is a primer that is complementary to a complementary strand of a template nucleic acid to which the mutant-type primer (Xmt) and the normal-type primer (Xwt) can be annealed (see FIG. 6). Therefore, for example, the mutant-type primer (Xmt) and the primer (Y2) as a pair of primers and the normal-type primer (Xwt) and the primer (Y2) as a pair of primers can amplify the template nucleic acid and the complementary strand thereto. Further, since the primer (Y2) is a primer that anneals to a region different from the objective base site to be detected, regardless of whether the base site is a mutant-type or a normal-type, the target nucleic acid sequence can be amplified. As described above, in a case where amplification is caused when the mutant-type primer (Xmt) is annealed to the normal-type base, or in a case where amplification is caused when the normal-type primer (Xwt) is annealed to the mutant-type base, the thus obtained amplification product has a sequence depending on each primer. However, by the use of the primer (Y2) in combination with the mutant-type primer (Xmt) or the normal-type primer (Xwt), an amplification product remaining an original sequence of the template nucleic acid can be also obtained. Thereby, reliability of the mutation detection can be further improved.

The length of the primer (Y2) is not particularly limited. However, normally, the length is preferably 10 to 50 bases, more preferably 15 to 40 bases, and particularly preferably 16 to 35 bases. Further, the primer (Y2) is applicable as long as it can anneal to a complementary sequence for a region on the 5' side relative to the base site in the template nucleic acid, the sequence thereof is not particularly limited, and can be designed according to known methods for designing a primer.

As described above, the template nucleic acid may be a single-stranded nucleic acid or a double-stranded nucleic acid. Examples of the template nucleic acid include DNAs; RNAs (such as total RNA, mRNA, and the like); and the like. Further, examples of the template nucleic acid include nucleic acids contained in samples such as a biological sample and the like. The nucleic acid in the sample may be a nucleic acid originally contained in a biological sample. For example, since accuracy of the mutation detection can be improved, an amplification product amplified by a nucleic acid amplification method using the nucleic acid in the biological sample as a template can be used. Specific examples thereof include an amplification product amplified by the nucleic acid amplification method using DNA originally contained in the biological sample as a template; an amplification product amplified by the nucleic acid amplification method using cDNA produced from RNA originally contained in the biological sample by RT-PCR (reverse transcription PCR) as a template; and the like. These amplification products may be the template nucleic acid of the present invention. The length of the amplification product is not particularly limited, however is, for example, 50 to 1000 bases and preferably 80 to 200 bases.

In the amplification step of the present invention, an example of amplification in the same reaction system includes amplification of a target nucleic acid sequence in one reaction solution.

In the amplification step of the present invention, it is preferable that an amplification reaction is performed using a nucleic acid in a sample as a template. The sample is not particularly limited as long as it contains a nucleic acid to serve as a template. However, for example, a sample containing a biological sample-derived nucleic acid can be used. Examples of the biological sample include whole blood, cells in the mouth (such as oral mucosa), somatic cells (such as nails and hairs), germ cells, expectoration, amniotic fluid, paraffin-embedded tissue, urine, gastric juice, gastric lavage fluid, and suspensions thereof. Further, as described above, a reaction solution, in which nucleic acid amplification is performed using a biological sample-derived nucleic acid as a template, can be used as a nucleic acid sample of the present invention, and an amplification product contained in the reaction solution can be used as a template nucleic acid.

Further, when the method of the present invention for amplifying a target nucleic acid sequence is applied to a method of the present invention for detecting a mutation of the present invention that will be described later, although the sample is not particularly limited, for example, the method is very effective for a sample containing a nucleic acid having an objective base site that is unknown whether a mutant-type or a normal-type, a sample containing a mutant type nucleic acid and a normal-type nucleic acid, a sample that may contain those, and the like. Derivation of nucleic acids such as DNA, RNA, and the like is not particularly limited, and examples thereof include cells such as various cancer cells and the like, virus, mitochondria, and the like. Since cells of cancer blood cells or the like contain cells having nucleic acids that show a mutant-type and cells having nucleic acids that show a normal-type, the aforementioned problems are more likely to be caused. Therefore, particularly, the method of the present invention for detecting a mutation is preferably applied to samples having nucleic acids showing a mutant-type and having nucleic acids showing a normal-type. For example, the method is preferably applied to biological samples such as cells of various cancers such as leukemia and the like, and specifically, the method is preferably applied to blood samples, leukemia cells, and the like. In the present invention, a method for collecting a sample, a method for preparing a nucleic acid, and the like are not limited and known methods can be employed.

Nucleic acids derived from the aforementioned biological samples can be isolated from the biological samples by known methods, for example. For isolation of genomic DNA from whole blood, a commercially available genomic DNA isolation kit (product name: GFX Genomic Blood DNA Purification kit, produced by GE Healthcare) or the like can be used.

The method of the present invention for amplifying a target nucleic acid sequence uses the aforementioned primers in the amplification step, and other steps and conditions are not limited. A nucleic acid amplification method in the amplification step is not particularly limited and examples thereof include a PCR (polymerase chain reaction) method, a NASBA (nucleic acid sequence based amplification) method, a TMA (transcription-mediated amplification) method, a SDA (strand displacement amplification) method, and the like. Among them, the PCR method is preferred. It is to be noted that conditions for the nucleic acid amplification method are not particularly limited and the nucleic acid amplification can be performed by known methods.

In the amplification step, the proportion of a nucleic acid sample to be added to a reaction system (for example, a reaction solution) for an amplification reaction is not particularly limited. As a specific example, when the nucleic acid sample is a biological sample (for example, a whole blood sample), the lower limit of the proportion of the nucleic acid sample to be added to the reaction system is, for example, preferably 0.01% by volume or more, more preferably 0.05% by volume or more, and further preferably 0.1% by volume or more. Further, the upper limit of the proportion of the nucleic acid sample to be added to the reaction system is not particularly limited. The upper limit is, for example, preferably 2% by volume or less, more preferably 1% by volume or less, and further preferably 0.5% by volume or less.

Further, in the detection of a mutation that will be described later, for example, when optical detection using a labeled probe is conducted, the proportion of the biological sample such as a whole blood sample to be added to the reaction system is preferably set, for example, in the range from 0.1% by volume to 0.5% by volume. Generally, in the PCR reaction, a heat treatment is carried out to denature DNA (i.e. to disassociate it into a single-stranded DNA). This heat treatment may denature, for example, sugar and protein contained in the sample and thereby may generate an insolubilized sediment or turbidity. Therefore, when the presence or absence of a mutation is checked by an optical method, the generation of such a sediment or turbidity may affect measurement accuracy. However, when the proportion of the whole blood sample to be added to the reaction system is set in the aforementioned range, for example, the effect of, for example, a generated sediment or the like due to denaturation can be prevented sufficiently and thereby the accuracy of measurement carried out by the optical method can be improved, although the mechanism thereof is unknown. Furthermore, since it also can sufficiently prevent PCR from being inhibited due to the contaminants contained in a whole blood sample, the amplification efficiency can be improved further. Therefore, by setting the proportion of the biological sample such as a whole blood sample to be added in the aforementioned range, for example, necessity of a pretreatment of the sample for preventing the generation of a sediment or turbidity or for removing them can be eliminated.

Furthermore, the proportion of the whole blood sample in the reaction system can be indicated as a weight percent of hemoglobin (hereinafter referred to as "Hb") instead of the aforementioned volume percent (for example, 0.1% by volume to 0.5% by volume). In this case, the proportion of the whole blood sample in the reaction system is, for example, preferably in the range from 0.565 g/L to 113 g/L, more preferably in the range from 2.825 g/L to 56.5 g/L, and further preferably in the range from 5.65 g/L to 28.25 g/L, in terms of the Hb amount. The proportion of the whole blood sample to be added to the reaction system may satisfy, for example, both the volume percent and the Hb weight percent, or may satisfy one of them. The whole blood may be any one of, for example, hemolyzed whole blood, unhemolyzed whole blood, anticoagulated whole blood, and whole blood containing coagulated fractions.

It is preferable that albumin is further added to the reaction system in advance of the start of an amplification reaction in the amplification step. Such addition of albumin further can reduce the effect of generation of sediment or turbidity described above and also further can improve the amplification efficiency.

The proportion of albumin to be added to the reaction system is, for example, in the range from 0.01% by weight to 2% by weight, preferably in the range from 0.1% by weight to 1% by weight, and more preferably in the range from 0.2% by weight to 0.8% by weight. The albumin is not particularly limited. Examples thereof include bovine serum albumin (BSA), human serum albumin, rat serum albumin, and horse serum albumin. One of them may be used alone or two or more of them may be used in combination.

Next, the method of the present invention for amplifying a target nucleic acid sequence will be explained with reference to a PCR method as an amplification method in the amplification step as an example. However, the present invention is not limited thereto. Further, conditions for PCR are not particularly limited and PCR can be performed by known methods.

First, a PCR reaction solution containing a template nucleic acid and the aforementioned respective primers is prepared. The proportions of the primers to be added to the PCR reaction solution are not particularly limited. The mutant-type primer (Xmt) is added to be, for example, preferably 0.01 µmol/L to 10 µmol/L, more preferably 0.05 µmol/L to 5 µmol/L, and particularly preferably 0.1 µmol/L to 1 µmol/L. The normal-type primer (Xwt) is added to be, for example, preferably 0.01 µmol/L to 10 µmol/L, more preferably 0.05 µmol/L to 5 µmol/L, and particularly preferably 0.1 µmol/L to 0.5 µmol/L. The molar ratio (Xmt:Xwt) between the mutant-type primer (Xmt) and the normal-type primer (Xwt) is, for example, preferably 1:0.001 to 1:10, more preferably 1:0.01 to 1:2, and particularly preferably 1:0.1 to 1:1.

Further, when the primer (Y2) is used in addition to the mutant-type primer (Xmt) and the normal-type primer (Xwt), the primer (Y2) is added to be, for example, preferably 0.01 µmol/L to 10 µmol/L, more preferably 0.05 µmol/L to 5 µmol/L, and particularly preferably 0.1 µmol/L to 1 µmol/L. The molar ratio (Xmt:Y2) between the mutant-type primer (Xmt) and the primer (Y2) is, for example, preferably 1:0.001 to 1:10, more preferably 1:0.01 to 1:2, and particularly preferably 1:0.1 to 1:1.

Other composition components in the reaction solution are not particularly limited. Known components can be used as the other composition components and the proportions thereof also are not particularly limited. Examples of the composition components include DNA polymerase; nucleotide such as nucleoside triphosphate (dNTP) and the like; solvents; and the like. In the reaction solution, the order of addition of the respective composition components is not limited by any means.

The DNA polymerase is not particularly limited and, for example, a known thermoduric bacteria-derived polymerase can be used. Specifically, for example, *Thermus aquaticus*-derived DNA polymerase (U.S. Pat. No. 4,889,818 and U.S. Pat. No. 5,079,352) (product name: Taq polymerase), *Thermus thermophilus*-derived DNA polymerase (WO 91/09950) (rTth DNA polymerase), *Pyrococcus furiosus*-derived DNA polymerase (WO 92/9689) (Pfu DNA polymerase; produced by Stratagene), and *Thermococcus litoralis*-derived DNA polymerase (EP 0455430) (Trademark; Vent; produced by New England Biolabs) are commercially available. Particularly, *Thermus aquaticus*-derived thermostable DNA polymerase is preferred.

The proportion of DNA polymerase to be added to the reaction solution is not particularly limited however is, for example, 1 U/mL to 100 U/mL, preferably 5 U/mL to 50 U/mL, and more preferably 20 U/mL to 30 U/mL. With respect to the unit of activity (U) of DNA polymerase, generally, 1 U denotes the activity that allows all 10 nmol of nucleotide to be taken into an acid-insoluble sediment in 30 minutes at 74° C. in a reaction solution for activity measurement, with an activated salmon sperm DNA being used as a template primer. The composition of the reaction solution for activity measurement is, for example, 25 mmol/L TAPS buffer (pH 9.3, 25° C.), 50 mmol/L KCl, 2 mmol/L $MgCl_2$, 1 mmol/L mercaptoethanol, 200 µmol/L dATP, 200 µmol/L dGTP, 200 µmol/L dTTP, 100 µmol/L [$\alpha$-$^{32}$P] dCTP, and 0.25 mg/mL activated salmon sperm DNA.

Generally, examples of the nucleoside triphosphate include dNTP (for example, dATP, dGTP, dCTP, dTTP, and dUTP). The proportion of dNTP to be added to the reaction solution is not particularly limited however is, for example, 0.01 mmol/L to 1 mmol/L, preferably 0.05 mmol/L to 0.5 mmol/L, and more preferably 0.1 mmol/L to 0.3 mmol/L.

Examples of the solvent include buffer solutions such as Tris-HCl, Tricine, MES, MOPS, HEPES, and CAPS. Commercially available PCR buffer solutions or buffer solutions of commercially available PCR kits can be used.

Furthermore, the PCR reaction solution further may contain glycerol, heparin, betaine, KCl, $MgCl_2$, $MgSO_4$, and the like. The proportions thereof to be added can be set in ranges in which the PCR reaction is not impaired.

The total volume of the reaction solution is not particularly limited and can be determined suitably according to, for example, the equipment (thermal cycler) to be used. It is generally 1 µL to 500 µL and preferably 10 µL to 100 µL.

Subsequently, PCR is performed. The PCR includes three steps of (1) dissociation of a double-stranded nucleic acid into a single-stranded nucleic acid, (2) annealing of a primer, and (3) elongation of a primer (polymerase reaction). Conditions for the respective steps are not particularly limited. The step (1) is performed, for example, preferably at 90° C. to 99° C. for 1 second to 120 seconds, and more preferably at 92° C. to 95° C. for 1 second to 60 seconds. The step (2) is performed, for example, preferably at 40° C. to 70° C. for 1 second to 300 seconds, and more preferably at 50° C. to 70° C. for 5 seconds to 60 seconds. The step (3) is performed, for example, preferably at 50° C. to 80° C. for 1 second to 300 seconds, and more preferably at 50° C. to 75° C. for 5 seconds to 60 seconds. Furthermore, the number of cycles also is not particularly limited but preferably is at least 30, with the aforementioned three steps (1) to (3) being considered as one cycle. The upper limit thereof, in total, is not particularly limited however is, for example, 100 cycles or less, preferably 70 cycles or less, and further preferably 50 cycles or less. The change in temperature in each step can be controlled automatically using, for example, a thermal cycler.

In the manner described above, a target nucleic acid sequence including an objective base site to be detected can be produced. In the present invention, more than one target nucleic acid sequence can be amplified simultaneously in one reaction solution. In this case, for respective target nucleic acid sequences, the mutant-type primer (Xmt), the normal-type primer (Xwt), and optionally the primer (Y2) are provided, and the aforementioned amplification reaction can be performed in the presence of these primers.

The method of the present invention for amplifying a target nucleic acid sequence may further include a step for detecting the amplification product obtained by the aforementioned amplification reaction. Thereby, for example, the presence or absence of the mutation of the objective base site in the target nucleic acid sequence can be detected. The detection of the mutation can be checked by the Tm analysis that will be described later. Specifically, for example, a probe capable of hybridizing to a sequence (hereinafter, also referred to as an "objective sequence to be detected") including the objective base site to be detected is further added to a reaction system of the amplification reaction in the amplification step. Further, the temperature of the reaction system is caused to be changed and a signal value that shows a molten state of a hybridization product between the amplification product and the probe is measured. From the change in the signal value accompanying the change in the temperature, the presence or absence of the mutation can be checked. The timing of addition of the probe is not particularly limited. The probe can be added to the reaction system in any stage, for example, before the amplification reaction, during the amplification reaction, or after the amplification reaction. Above all, it is preferable that the probe is added before the amplification reaction. The detection of the mutation will be explained specifically in the method of the present invention for detecting a mutation that will be described later. Further, the probe and the like are also as described later.

Second Embodiment

In the second method of the present invention for amplifying a target nucleic acid sequence, for example, the second amplification reagent containing the primer (Xmt) and a primer (Y1) is used. Specifically, the amplification step is a step for amplifying the target nucleic acid sequence using the primer (Xmt) and the primer (Y1) in the same reaction system.

Primer (Y1)

Figure 7:
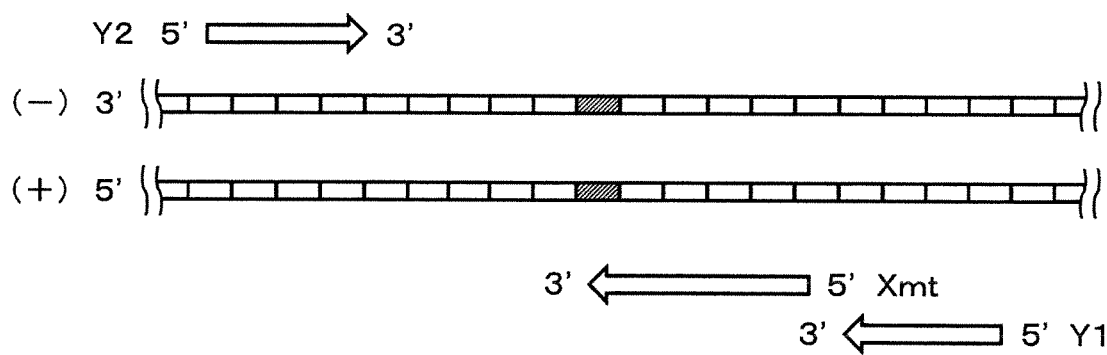
FIG. 7 is a schematic showing the relationship between a primer and a template nucleic acid in another embodiment of the present invention.

Primer that is complementary to a region at a 3' side relative to the base site in the template nucleic acid The primer (Xmt) in this embodiment is the same as that in the first embodiment. Further, this embodiment can be performed in the same manner as in the first embodiment, unless otherwise mentioned. As described above, the template nucleic acid may be a single-stranded nucleic acid or a double-stranded nucleic acid. When the template nucleic acid is a double-stranded nucleic acid, for example, it is preferable to design the mutant-type primer (Xmt) and the primer (Y1) so as to be complementary to either one of the single-stranded nucleic acids of the double-stranded nucleic acid. Further, for example, it is preferable to design the aforementioned primer (Y2) so as to be complementary to the other of the single-stranded nucleic acids. A schematic of FIG. 7 shows an example of the relationship between a template nucleic acid and a primer. In FIG. 7, (+) and (−) each indicate a single-stranded nucleic acid of a double-stranded template nucleic acid, and the shaded areas indicate the objective base sites to be detected. As shown in FIG. 7, the mutant-type primer (Xmt) and the primer (Y1) are both designed as primers that are complementary to the (+) strand. In this case, it is preferable that the primer (Y2) is designed as a primer that is complementary to the (−) strand. It is to be noted that FIG. 7 is a schematic showing a mere example and does not limit, for example, the length of each primer and the annealing region in the template nucleic acid, and the primer (Y2) is also optional. Further, the mutant-type primer (Xmt) and the primer (Y1) may both be designed as primers that are complementary to the (−) strand, and the primer (Y2) may be designed as a primer that is complementary to the (+) strand.

According to this embodiment, the use of the mutant-type primer (Xmt) and the primer (Y1) allows the following, for example. That is, even when the template nucleic acid includes a normal-type template nucleic acid and a mutant-type template nucleic acid and the content of the mutant-type template nucleic acid is low, since an affinity of the mutant-type primer (Xmt) with reference to the mutant-type template nucleic acid is higher than that with reference to the normal-type template nucleic acid, a low content of the mutant-type template nucleic acid can be amplified efficiently. On the other hand, since the primer (Y1) is a primer that anneals to a region different from the objective base site to be detected, regardless of whether the base site is a mutant-type or a normal-type, the target nucleic acid sequence can be amplified. Therefore, the mutant-type template nucleic acid is further amplified also by the primer (Y1). Therefore, even with a low content of the mutant-type template nucleic acid, for example, an amplification product of the degree capable of being detected in the Tm analysis that will be described later can be obtained, and the mutant-type template nucleic acid can be detected. Further, the normal-type template nucleic acid is also amplified with the primer (Y1) and the normal-type can be detected by the Tm analysis. Furthermore, also in the case where the template nucleic acid only includes a mutant-type template nucleic acid, in the same manner, the amplification can be performed with the mutant-type primer (Xmt) and the primer (Y1). Moreover, even when the template nucleic acid only includes a normal-type template nucleic acid, since the target nucleic acid sequence whose objective base site to be detected is a normal-type base can be amplified with this primer (Y1), also with respect to the normal-type template nucleic acid, analysis of the normal-type can be conducted by the Tm analysis that will be described later.

Further, by the use of the primer (Y1), an amplification product retaining an original sequence of the template nucleic acid can be obtained. That is, for example, in a case where amplification is caused when the mutant-type primer (Xmt) is annealed to the normal-type template nucleic acid, the thus obtained amplification product has a sequence depending on the mutant-type primer (Xmt). However, by the use of the primer (Y1) in combination with the mutant-type primer (Xmt), an amplification product remaining an original sequence of the template nucleic acid can be also obtained. Thereby, it can be prevented that only the amplification product mistakenly obtained is increased and reliability of the mutation detection can be improved.

The length of the primer (Y1) is not particularly limited. Normally, the length is preferably 10 to 50 bases, more preferably 15 to 40 bases, and particularly preferably 16 to 35 bases. Further, the primer (Y1) is applicable as long as it can anneal to a region on the 3' side relative to the base site in the template nucleic acid, the sequence thereof is not particularly limited, and can be designed according to known methods for designing a primer.

The proportions of the primers to be added to the reaction solution are not particularly limited. The mutant-type primer (Xmt) is added to be, for example, preferably 0.01 µmol/L to 10 µmol/L, more preferably 0.05 µmol/L to 5 µmol/L, and particularly preferably 0.1 µmol/L to 1 µmol/L. The primer (Y1) is added to be, for example, preferably 0.01 µmol/L to 10 µmol/L, more preferably 0.05 µmol/L to 5 µmol/L, and particularly preferably 0.1 µmol/L to 1 µmol/L. The molar ratio (Xmt:Y1) between the mutant-type primer (Xmt) and the primer (Y1) is, for example, preferably 1:0.001 to 1:10, more preferably 1:0.01 to 1:2, and particularly preferably 1:0.1 to 1:1. Further, it is preferable to use a primer (Y2) in the same manner as in the first embodiment.

Third Embodiment

In the third method of the present invention for amplifying a target nucleic acid sequence, for example, the amplification step is a step for amplifying the target nucleic acid sequence using the primer (Xmt) and 3'-5 exonuclease in the reaction system.

The primer (Xmt) in this embodiment is the same as that in the first embodiment. Further, this embodiment can be performed in the same manner as in the aforementioned respective embodiments, unless otherwise mentioned.

According to this embodiment, the amplification reaction using the mutant-type primer (Xmt) in the presence of the exonuclease allows the following, for example. That is, when the template nucleic acid includes a normal-type template nucleic acid and a mutant-type template nucleic acid, it can be considered that the mutant-type primer (Xmt) anneals not only to the mutant-type template nucleic acid but also to the normal-type template nucleic acid to synthesize an elongated strand. However, since the mutant-type primer (Xmt) is a primer not complementary to the normal-type template nucleic acid but complementary to the mutant-type template nucleic acid, even when the mutant-type primer (Xmt) is annealed to the normal-type template nucleic acid, mismatching occurs at least at the objective base site to be detected, and reactivity thereof is inferior to that of the elongation reaction to the mutant-type template nucleic acid. Therefore, even when both the normal-type template nucleic acid and the mutant-type template nucleic acid are present, the mutant-type template nucleic acid can be amplified preferentially. On the other hand, with respect to the mutant-type primer (Xmt) annealed to the normal-type template nucleic acid, since the 3' region thereof (i.e., a region including a corresponding base of a mutant-type base) mismatches with the normal-type template nucleic acid, the aforementioned region is in a state of being single-stranded without being annealed. When this single-stranded region is cleaved with 3'→5' exonuclease, a sequence complementary to a normal-type template sequence is amplified. Since the thus obtained amplification product has a normal-type target nucleic acid sequence, when a template nucleic acid includes a normal-type template nucleic acid, the normal-type template nucleic acid can also be detected with the amplification product from the mutant-type primer (Xmt).

The proportion of the mutant-type primer (Xmt) to be added to a reaction solution for an amplification reaction is not particularly limited. However, the mutant-type primer (Xmt) is added to be, for example, preferably 0.001 μmol/L to 10 μmol/L, more preferably 0.01 μmol/L to 5 μmol/L, and particularly preferably 0.1 μmol/L to 1 μmol/L. Further, 3'→5' exonuclease is not particularly limited. It is preferable that polymerase used for the amplification reaction has this catalytic activity. Examples of the polymerase having 3'→5' exonuclease activity include Pfu polymerase, polymerase, KOD polymerase, Vent polymerase, Tgo polymerase, and the like. Further, as in the case of the first embodiment or the second embodiment, one of the primer (Y1), the primer (Y2), and the primer (Xwt) may be used alone or two or more of them may be used in combination.

<Amplification Reagent>

The amplification reagent of the present invention is an amplification reagent used for the method of the present invention for amplifying a target nucleic acid sequence. The first amplification reagent of the present invention contains the primer (Xmt) and the primer (Xwt), and the second amplification reagent contains the primer (Xmt) and the primer (Y1).

The first amplification reagent of the present invention can be used, for example, for the first embodiment of the method of the present invention for amplifying a target nucleic acid sequence. The second amplification reagent of the present invention can be used, for example, for the second embodiment of the method of the present invention for amplifying a target nucleic acid sequence. Further, it is preferable that the first amplification reagent and the second amplification reagent of the present invention further contain the primer (Y2). In the present invention, the respective primers are as described above.

The third amplification reagent of the present invention contains the primer (Xmt) and 3'→5' exonuclease. The third amplification reagent of the present invention can be used, for example, for the third embodiment of the method of the present invention for amplifying a target nucleic acid sequence. The third amplification reagent of the present invention may further contain one of or less than three of the primer (Y1), the primer (Y2), and the primer (Xwt).

In the amplification reagent of the present invention, the aforementioned respective primers are as described above. The amplification reagent of the present invention may further contain various components used for an amplification reaction described in the method of the present invention for amplifying a target nucleic acid sequence, for example. It is preferable that the amplification reagent of the present invention is used in one reaction system. Further, the amplification reagent of the present invention may be an amplification kit used for the method of the present invention for amplifying a target nucleic acid sequence, and the components each may be contained in an independent container or they may be contained in the same container in an appropriate combination. It is preferable that the amplification kit has, for example, an instruction manual.

<Method for Detecting Mutation>

As described above, the method of the present invention for detecting a mutation is a method for detecting the presence or absence of a mutation of an objective base site to be detected in a template nucleic acid, including steps of:

(a) amplifying a target nucleic acid sequence including the base site in the template nucleic acid by the method of the present invention for amplifying a target nucleic acid sequence in a reaction system;

(b) changing a temperature of the reaction system containing an amplification product obtained in the step (a) in the presence of a probe capable of hybridizing to a sequence including the base site in the template nucleic acid and measuring a signal value that shows a molten state of a hybridization product between the amplification product and the probe; and (c) determining the presence or absence of the mutation of the objective base site from a change in the signal value accompanying a change in the temperature.

The present invention amplifies target nucleic acid sequences by the aforementioned methods and conducts the so-called Tm analysis, and other steps and conditions are not limited at all. In the present invention, examples of a "mutation" include SNPs and the like.

The present invention is preferably applied to samples containing nucleic acids. The sample is not particularly limited and the samples as described above can be used. Further, the type of the template nucleic acid is not particularly limited and the template nucleic acids as described above can be used.

The probe for detecting a mutation (hereinafter, also referred to as a "detection probe") is not particularly limited and can be designed by known methods. For example, when the template nucleic acid is a double-stranded template nucleic acid, the probe may be designed so as to hybridize to an objective sequence to be detected of a sense strand (a probe for detecting a sense strand) or to hybridize to an objective sequence to be detected of an antisense strand (a probe for detecting an antisense strand). Further, when the probe is designed, the objective base site to be detected in the objective sequence to be detected may be designed as a normal-type base or a mutant-type base. That is, when the detection probe is annealed to the objective sequence to be detected, a base corresponding to the objective base site to be detected in the objective sequence to be detected may be complementary to a normal-type base or complementary to a mutant-type base. Since the present invention is intended to detect, particularly, a mutant-type base, for example, in the aforementioned probe, it is preferable that a base corresponding to the objective base site to be detected is complementary to a mutant-type base and not complementary to a normal-type base.

In the present invention, as described above, the detection probe is applicable as long as the probe can hybridize to the objective sequence to be detected including the objective base site. The sequence of the probe is not particularly limited. For example, at the time of forming hybrid, excluding a site (base) being paired with the objective base site to be detected (i.e., a site where an objective mutation occurs), the probe preferably has the sequence 90% to 100% identical to the complementary sequence to the objective sequence to be detected and particularly preferably has the sequence 100% identical to the complementary sequence to the objective sequence to be detected.

The proportion of the probe to be added to the reaction system is not particularly limited. The probe is added to be, for example, preferably 10 nmol/L to 400 nmol/L, and more preferably 20 nmol/L to 200 nmol/L. Further, when the probe is a labeled probe labeled with a labeling substance such as a fluorescent dye or the like, for example, in order to adjust signal intensity such as fluorescence intensity to be detected, an unlabeled probe with a sequence identical to that of the labeled probe may be used in combination. The unlabeled probe may include a phosphate group added to the 3' end thereof. In this case, the molar ratio between the labeled probe and the unlabeled probe is preferably, for example, 1:10 to 10:1. The length of the probe is not particularly limited. It is, for example, a 5- to 50-mer and preferably a 10- to 30-mer.

The probe can be added to a reaction system for an amplification reaction after the step (a), i.e., after performing an amplification reaction of a target nucleic acid sequence. However, since analysis can be conducted easily and promptly, it is preferable that the probe is preliminarily added to the reaction system in advance of the amplification reaction of the step (a). It is to be noted that the proportions of respective primers to be added to the reaction solution are as described above. When the probe is added to the reaction system in advance of the amplification reaction in this manner, for example, in order to prevent elongation of the probe itself, the probe may further include a phosphate group added to the 3' end thereof or the probe may be labeled with a fluorescent dye at the 3' end thereof.

The Tm value is explained. When a solution containing double-stranded DNA is heated, the absorbance at 260 nm increases. This is because heating releases the hydrogen bonds between both strands in the double-stranded DNA to dissociate it into single-stranded DNA (i.e. DNA melting). When all double-stranded DNAs are dissociated into single-stranded DNAs, the absorbance thereof indicates approximately 1.5 times the absorbance (i.e. absorbance of only double-stranded DNAs) obtained at the start of heating, which makes it possible to judge that melting is completed. Based on this phenomenon, the melting temperature Tm is generally defined as a temperature at which the absorbance has reached 50% of the total increase in absorbance.

In the aforementioned step (b), the measurement of the signal value that indicates the molten state of the hybridization product between the amplification product and the probe may be a measurement of absorbance at 260 nm as described above or may be a measurement of the signal of a labeling substance. Specifically, it is preferable that a labeled probe labeled with a labeling substance is used as the aforementioned probe to perform the measurement of the signal of the labeling substance. The labeled probe can be, for example, a labeled probe that exhibits a signal independently but does not exhibit a signal by hybridization, or a labeled probe that does not exhibit a signal independently but exhibits a signal by hybridization. The former probe does not exhibit a signal when the probe forms a hybrid (for example, double-stranded DNA) with an objective sequence to be detected but exhibits a signal when the probe is released by heating. On the other hand, the latter probe exhibits a signal when the probe forms a hybrid (for example, double-stranded DNA) with an objective sequence to be detected, but the signal is reduced (quenched) when the probe is released by heating. Accordingly, when the signal exhibited by the label is detected under a condition (absorption wavelength etc.) specific to the signal, the progress of melting of the hybridization product and the Tm value can be determined as in the case of the measurement of absorbance at 260 nm.

As described above, in the step (a), more than one target nucleic acid sequence can be amplified simultaneously in the same reaction solution. Further, with respect to amplification products, respective objective mutations can be checked. In this case, for each objective sequence to be detected including a base site where an objective mutation occurs, the probe hybridizing thereto may be provided. As such probes, it is preferable to use labeled probes labeled with different labeling substances to be detected under different conditions. By using such probes, even in the same reaction system, respective mutations can be detected by changing detection conditions.

Specific examples of the labeling substance in the labeled probe include a fluorescent dye and a fluorophore. A specific example of the labeled probe is preferably a probe that is labeled with a fluorescent dye, exhibits fluorescence independently, and allows fluorescence to be reduced (for example, quenched) by hybridization. A probe that utilizes such a fluorescence quenching phenomenon is generally called a fluorescence quenching probe. Above all, as the probe, a base at the 3' region (for example, the 3' end) of oligonucleotide or the 5' region (for example, the 5' end) of oligonucleotide is preferably labeled with a fluorescent dye, and the base to be labeled is preferably cytosine (C). In this case, in an objective sequence to be detected to which the labeled probe is hybridized, it is preferable to design a base sequence of the labeled probe that a base being paired with the end base C of the labeled probe or a base one to three bases away from the base being paired with the end base C of the labeled probe is guanine (G). Such a probe is generally called as a guanine quenching probe and is known as the so-called Qprobe®. When such a guanine quenching probe hybridizes to an objective sequence to be detected, the phenomenon in which emission of the fluorescent dye decreases (fluorescence intensity decreases) when the end base C thereof labeled with the fluorescent dye approaches G in the objective sequence to be detected occurs. The use of such a probe makes it possible to check hybridization and dissociation easily on the basis of the change in the signal. Further, normally, the labeling substance can be bound to a phosphate group of nucleotide, for example.

The fluorescent dye is not particularly limited. Examples thereof include fluorescein, phosphor, rhodamine, a polymethine dye derivative, and the like. Examples of the commercially available fluorescent dye include BODIPY FL (trade mark, produced by Molecular Probe Inc.), FluorePrime (product name, produced by Amersham Pharmacia), Fluoredite (product name, produced by Millipore Corporation), FAM (produced by ABI), Cy3 and Cy5 (produced by Amersham Pharmacia), TAMRA (produced by Molecular Probe Inc.), and the like. The combination of fluorescent dyes used for plural probes is not particularly limited as long as it can be detected under different conditions, for example. An example of the combination includes Pacific Blue (detection wavelength of 450 nm to 480 nm), TAMRA (detection wavelength of 585 nm to 700 nm), and BODIPY FL (detection wavelength of 515 nm to 555 nm).

Next, the method of the present invention for detecting a mutation will be explained with reference to a method in which a nucleic acid is amplified by PCR and a labeled probe is used as a detection probe as an example. However, the present invention is not limited thereto.

First, PCR is performed as described above using a reaction solution in which a sample containing a template nucleic acid, the aforementioned primers of the present invention, and a labeled probe that hybridizes to the objective sequence to be detected are added. Besides the aforementioned primers and the labeled probe, the reaction solution may contain various additives that can be used for amplifying, for example, DNA polymerase, dNTP, and other nucleic acids.

The timing of addition of the labeled probe is not particularly limited. The probe can be added, for example, before the amplification reaction, during the amplification reaction, or after the amplification reaction. However, since the amplification reaction of the step (a) and the step (b) can be performed continuously, it is preferable that the probe is added before the amplification reaction.

Next, the amplification product thus obtained is dissociated and then single-stranded DNA obtained through dissociation is hybridized with the labeled probe. This can be carried out, for example, by changing the temperature of the reaction solution.

The heating temperature in the dissociation step is not particularly limited as long as it allows the amplification products to be dissociated. It is, for example, 85° C. to 95° C. The heating time also is not particularly limited and generally is 1 second to 10 minutes and preferably 1 second to 5 minutes.

The dissociated single-stranded DNA can be hybridized with the labeled probe, for example, by decreasing the heating temperature employed in the dissociation step after the dissociation step. The temperature condition is, for example, 40° C. to 50° C.

The temperature of the reaction solution is caused to be changed and thereby the signal value that indicates the molten state of the hybridization product between the amplification product and the labeled probe is measured. Specifically, for example, the reaction solution is heated, i.e., the hybridization product between the single-stranded DNA and the labeled probe is heated, and the change in the signal value accompanying the temperature rise is measured. As described above, for example, when a probe (guanine quenching probe), in which the base C at the end is labeled, is used, fluorescence decreases (or quenches) in the state where the probe is hybridized with the single-stranded DNA, while fluorescence is emitted in the state where the probe is dissociated. Accordingly, for example, the hybridization product in which the fluorescence has decreased (or been quenched) may be heated gradually and the increase in fluorescence intensity accompanying the temperature rise may be measured. It is to be noted that when the labeled probe is used, the signal value can be measured under the condition corresponding to the labeling substance of the labeled probe. When plural objective bases to be detected are present and mutations are detected using plural types of probes, as described above, respective signal values may be measured using probes labeled with labeling substances of different detection conditions under the conditions corresponding to the labeling substances of the respective probes.

The temperature range in which the change in fluorescence intensity is to be measured is not particularly limited. The start temperature is, for example, room temperature to 85° C. and preferably 25° C. to 70° C., while the end temperature is, for example, 40° C. to 105° C. Furthermore, the rate of temperature rise is not particularly limited however is, for example, 0.1° C./sec to 20° C./sec and preferably 0.3° C./sec to 5° C./sec.

Next, the Tm value is determined by analyzing the change in the signal. Specifically, the amount of change in the fluorescence intensity per unit time at each temperature is calculated from the fluorescence intensity obtained. When the amount of change is "−d fluorescence intensity increase/dt", the temperature at which the lowest value is obtained can be determined as the Tm value, for example. Further, when the amount of change is "d fluorescence intensity increase/t", the point at which the amount of increase is the highest can be determined as the Tm value, for example. In contrast, the amount of decrease in the fluorescence intensity is measured when the labeled probe used is not a quenching probe but a probe that does not exhibit a signal independently but exhibits a signal by hybridization.

The Tm value can be calculated by using, for example, known MELTCALC software (www.meltcalc.com/) or also can be determined by the nearest neighbor method.

From these Tm values, the type of the base in the objective base site, i.e., the genotype such as a mutant-type or a normal-type in the objective base site is determined. In the Tm analysis, the case of a perfectly complementary hybrid (match) results in a higher Tm value indicating dissociation than that obtained in the case of a hybrid including a different single base (mismatch). Accordingly, with respect to the probe, when the Tm value obtained in the case of a perfectly complementary hybrid and the Tm value obtained in the case of a hybrid including a different single base are determined beforehand, the genotype at the objective base site can be determined. For example, in the case where the base located at the objective base site is assumed to be of a mutant-type, when a probe that is complementary to the objective sequence to be detected containing the mutant-type base is used, the objective base can be judged as a mutant-type if the Tm value of the resultant hybrid is equal to the Tm value of a perfectly complementary hybrid. Furthermore, the objective base can be judged as a normal-type if the Tm value of the resultant hybrid is equal to the Tm value of the hybrid including a different single base (i.e. a lower value than the Tm value of the perfectly complementary hybrid). Moreover, when both the Tm values are detected, it can be judged that both the nucleic acid that shows a mutant-type and the nucleic acid that shows a normal-type are present.

In the present invention, for example, a change in the signal during hybridization may be measured instead of the method in which the temperature of a reaction solution containing the probes is caused to be increased i.e., a hybridization product is heated and a change in the signal accompanying the temperature rise is measured as described above. In other words, when the temperature of the reaction solution containing the aforementioned probes is caused to be decreased to form hybridization products, the change in the signal accompanying the temperature decrease may be measured.

Specifically, when a labeled probe that exhibits a signal independently but does not exhibit a signal by hybridization (for example, a guanine quenching probe) is used, the labeled probe emits fluorescence in the state where single-stranded DNA and the probe are dissociated, but the fluorescence decreases (or quenches) when a hybrid is formed through temperature decrease. Accordingly, for example, the temperature of the reaction solution is caused to be decreased gradually and the decrease in fluorescence intensity accompanying the temperature decrease may be measured. On the other hand, when a labeled probe that does not exhibit a signal independently but exhibits a signal by hybridization is used, the labeled probe does not emit fluorescence in the state where single-stranded DNA and the probe are dissociated, but emits the fluorescence when a hybrid is formed through temperature decrease. Accordingly, for example, the temperature of the reaction solution is caused to be decreased gradually and the increase in fluorescence intensity accompanying the temperature decrease may be measured.

In the present invention, a nucleic acid in the sample may be a single-stranded nucleic acid or a double-stranded nucleic acid. When the nucleic acid is a double-stranded nucleic acid, for example, it is preferable to include a step for disassociating the double-stranded nucleic acid in the sample by heating in advance of the hybridization in step (b). When the double-stranded nucleic acid is disassociated into a single-stranded nucleic acid, the hybridization with the detection probe can be performed efficiently in the next step (b).

<Mutation Detection Reagent>

The mutation detection reagent of the present invention is a detection reagent used for the method of the present invention for detecting a mutation, and the detection reagent contains the amplification reagent of the present invention and a probe capable of hybridizing to a sequence including an objective base site to be detected in a template nucleic acid. It is preferable that the amplification reagent of the present invention is used in one reaction system.

It is to be noted that the mutation detection reagent of the present invention may further contain various components used for an amplification reaction described in the method of the present invention for detecting a mutation, for example. Further, the mutation detection reagent of the present invention may be the mutation detection kit of the present invention. It is preferable that the mutation detection kit has, for example, an instruction manual.

Next, Examples of the present invention are described. However, the present invention is not limited by the Examples.

EXAMPLES

Example 1

According to the first embodiment, a point mutation (C→T) of the 944$^{th}$ base of the bcr-abl gene is detected by the Tm analysis.

First, a normal-type plasmid (hereinafter, referred to as "wt") into which a normal-type bcr-abl gene sequence that does not have a mutation at the 944$^{th}$ base C is inserted and a mutant-type plasmid (hereinafter, referred to as "mt") into which a mutant-type bcr-abl gene whose 944$^{th}$ base C is mutated to T is inserted were provided. Both plasmids were mixed at predetermined proportions and thereby prepared plural nucleic acid samples. The mt contents in the plural nucleic acid samples were 100%, 10%, 5%, 3%, 1%, 0.5%, 0.3%, and 0%. In a tube, 1 µL ($2\times10^4$ copies/test) of the nucleic acid sample and 24 of the PCR reaction solution shown in the following table 1 were added, and PCR was conducted using a thermal cycler (product name: Mastercycler ep gradient S, produced by Eppendorf). In PCR, after treating at 95° C. for 60 seconds, one cycle of treatment at 99° C. for 4 seconds and at 66° C. for 30 seconds was repeated for 50 cycles. Further, the tube containing the PCR reaction solution was transferred to iCycler (product name, produced by Bio-Rad Laboratories, Inc.), treatments at 95° C. for 5 seconds and at 40° C. for 60 seconds were performed, one cycle of step in which the temperature is caused to be increased by 1° C. and incubated for 15 seconds was repeated for 55 cycles, and the PCR reaction solution was heated from 40° C. to 95° C. During the 55 cycles, the change in fluorescence intensity (detection wavelength of 515 nm to 545 nm) at each temperature from 40° C. to 75° C. was measured and the Tm analysis was conducted.

TABLE 1

| (PCR reaction solution composition) | |
|---|---|
| $H_2O$ | 17.94 µL |
| buffer*[1] | 2.5 µL |
| 80% glycerol | 1.56 µL |
| 2.5 mmol/L dNTP | 2.0 µL |
| 100 µmol/L sense primer (Y2) | 0.25 µL |
| 100 µmol/L normal-type primer (Xwt) | 0.063 µL |
| 100 µmol/L mutant-type primer (Xmt) | 0.063 µL |
| 5 µmol/L detection probe | 0.25 µL |
| 20 wt % BSA | 0.25 µL |
| 5 U/µL Gene Taq FP*[2] | 0.125 µL |
| Total | 24 µL |

*[1]10 x Gene Taq Universal Buffer (produced by Nippon Gene Co., Ltd.) (hereinafter, the same applies)
*[2]produced by Nippon Gene Co., Ltd. (hereinafter, the same applies)

The primer (Y2) is a sense primer in PCR and the normal-type primer (Xwt) and the mutant-type primer (Xmt) are antisense primers in PCR. The sequences of these primers are as follows. The normal-type primer (Xwt) is a complementary sequence 100% matching with a region including the 944$^{th}$ base (C) in a normal-type bcr-abl gene, and the mutant-type primer (Xmt) is a complementary sequence 100% matching with a region including the 944$^{th}$ base (T) in a mutant-type bcr-abl gene in which the 944$^{th}$ base C is mutated into T. It is to be noted that in the sequences of the normal-type primer (Xwt) and the mutant-type primer (Xmt), the bases at the 3' end written in capital letters respectively correspond to the 944$^{th}$ base of the normal-type bcr-abl gene and the 944$^{th}$ base of the mutant-type bcr-abl gene. The positional relationship among the normal-type primer (Xwt), the mutant-type primer (Xmt), and the sense strand to which these primers are annealed and the positional relationship between the sense primer (Y2) and the antisense strand to which this primer is annealed can be seen in the schematic of FIG. 6. However, this is merely an exemplary scheme and does not limit the present invention.

```
                                         SEQ ID NO: 1
Sense primer (Y2)
5'-ggacggacggaccgtcctcgttgtcttgttggc-3'

SEQ ID NO: 2
Normal-type primer (Xwt)
5'-ttcccgtaggtcatgaactcaG-3'

SEQ ID NO: 3
Mutant-type primer (Xmt)
5'-aggttcccgtaggtcatgaactcaA-3'
```

Further, the sequence of the detection probe used for the Tm analysis is shown as follows. The detection probe is a complementary sequence 100% matching with a region including the 944$^{th}$ base in the mutant-type bcr-abl gene (sense strand) in which the 944$^{th}$ base C is mutated into T. In the following sequence, the base A written as a capital letter corresponds to the 944$^{th}$ mutated base T. Further, P at the 3' end indicates a phosphate group.

SEQ ID NO: 4
Detection probe
5'-(BODIPY FL)-ctcaAtgatgatatagaacg-P-3'

The results thereof are shown in FIG. 1. FIG. 1 shows graphs of the Tm analysis that show the change in fluorescence intensity accompanying the temperature rise. The horizontal axes indicate the temperature (° C.) at the time of measurement. The vertical axes indicate the change in fluorescence intensity (hereinafter, also referred to as "fluorescence change amount") and "−d fluorescence intensity increase/dt" was used as the unit. As shown in FIG. 1, the peak of mt 100% (wt 0%), i.e., the Tm, was 55° C. and the peak of wt 100% (mt 0%), i.e., the Tm, was 47° C. With these as evaluation criteria of mt and wt, peaks of the Tm value of mt and the Tm value of wt with respect to respective samples were obtained. With respect to all samples in which mt and wt are present (mt 0.3% to 10%), although the amounts of mt were less than those of wt, peaks of the Tm value of mt could be observed.

Comparative Example 1

The Tm analysis was conducted in the same manner as in Example 1 except that 0.126 μL of the following 100 μmol/L primer was used as the antisense primer instead of the normal-type primer (Xwt) and the mutant-type primer (Xmt) and the conditions for PCR were changed as follows. That is, after treating at 95° C. for 60 seconds, one cycle of treatment at 99° C. for 4 seconds and at 62° C. for 30 seconds was repeated for 50 cycles. Since the sense primer (Y2) and the following antisense primer anneal to a region different from the 944$^{th}$ base of the bcr-abl gene, regardless of whether the 944$^{th}$ base is a normal base (C) or a mutant base (T), a region including the 944$^{th}$ base is amplified.

SEQ ID NO: 5
Antisense primer
5'-ggacggacggaccgcactccctcaggtagtcag-3'

Figure 2:
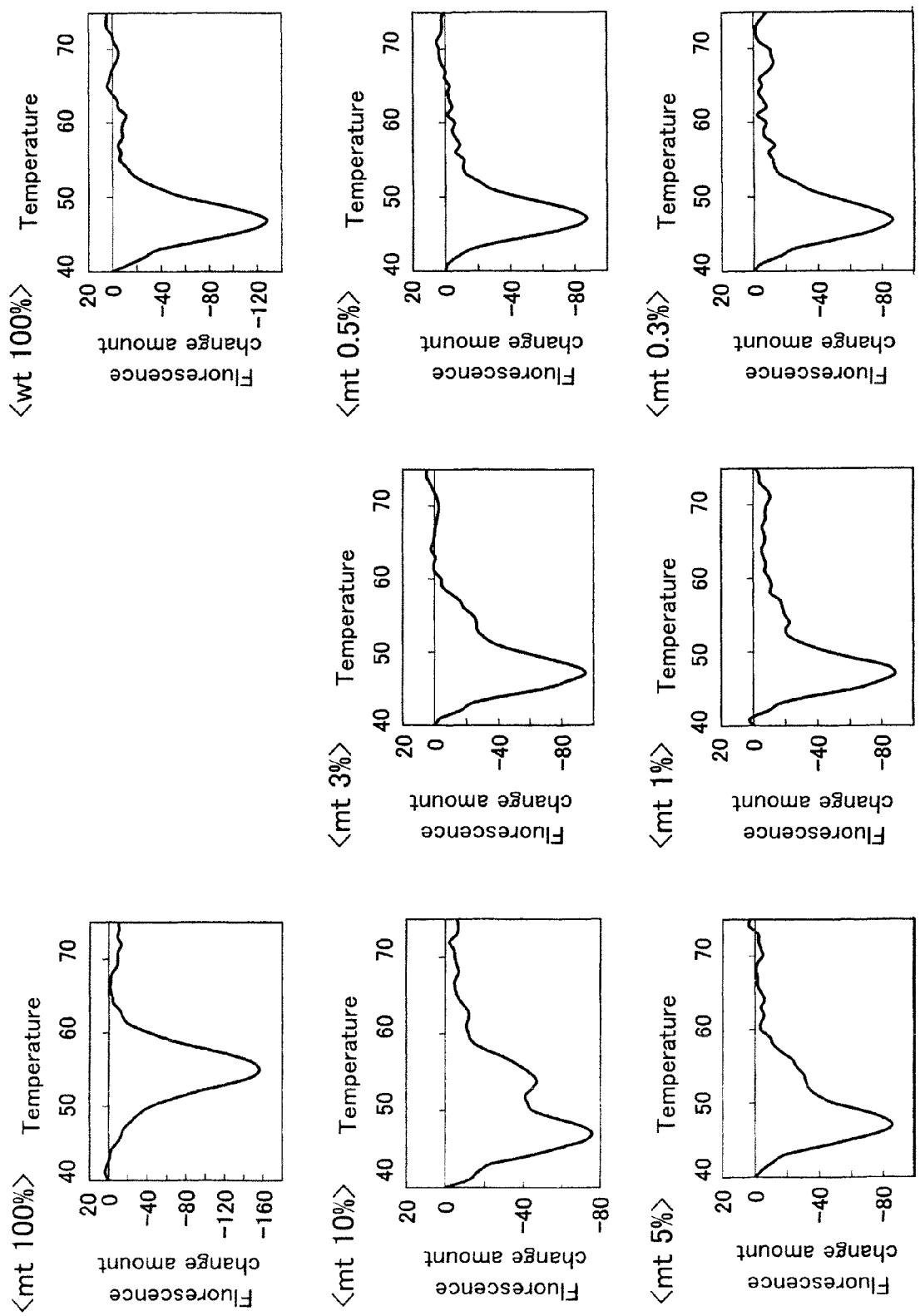
FIG. 2 includes graphs showing the results of Tm analysis in Comparative Example 1.

The results thereof are shown in FIG. 2. FIG. 2 shows graphs of the Tm analysis that show the change in fluorescence intensity accompanying the temperature rise. The horizontal axes indicate the temperature (° C.) at the time of measurement. The vertical axes indicate the change in fluorescence intensity (hereinafter, also referred to as "fluorescence change amount") and "−d fluorescence intensity increase/dt" was used as the unit. As shown in FIG. 2, the peak of mt 100% (wt 0%), i.e., the Tm, was 55° C. and the peak of wt 100% (mt 0%), i.e., the Tm, was 47° C. With these as evaluation criteria of mt and wt, peaks of the Tm value of mt and the Tm value of wt with respect to respective samples were obtained. With respect to the samples in which mt and wt are present, peaks of the Tm value of mt could be observed when mt is 10% or more, whereas the peak could not be observed when mt is less than 10%. The results showed that the method of Example 1 could achieve detection sensitivity superior to that of Comparative Example 1.

Comparative Example 2

A point mutation (C→T) at the 944$^{th}$ base of the bcr-abl gene was detected by a conventional ASP-PCR method.

In comparative Example 2, a wt reaction solution for amplifying wt whose 944$^{th}$ base is normal and a mt reaction solution for amplifying mt whose 944$^{th}$ base is mutated were prepared. The composition of these reaction solutions is shown as follows. The wt reaction solution used the normal-type primer (Xwt) of Example 1 as the antisense primer and the mt reaction solution used the mutant-type primer (Xmt) of Example 1 as the antisense primer. It is to be noted that the primer (Y2) was used as the sense primer in the same manner as in Example 1.

TABLE 2

| (ASP-PCR reaction solution composition) | |
|---|---|
| H$_2$O | 16.3125 μL |
| buffer*$^1$ | 2.5 μL |
| 80% glycerol | 1.5625 μL |
| 2.5 mmol/L dNTP | 2.0 μL |
| 100 μmol/L sense primer | 0.125 μL |
| 100 μmol/L antisense primer | 0.125 μL |
| 10xSYBR Green*$^3$ | 1.0 μL |
| 20 wt % BSA | 0.25 μL |
| 5 U/μL Gene Taq FP*$^2$ | 0.125 μL |
| Total | 24 μL |

*$^3$produced by TAKARA BIO INC.

In a tube, 1 μL (2×10$^4$ copies/test) of the nucleic acid sample that is the same sample used in Example 1 and 24 μL of the ASP-PCR reaction solution (wt reaction solution or mt reaction solution) shown in the following table 2 were added, and real-time PCR was conducted using the iCycler. In real-time PCR, after treating at 95° C. for 60 seconds, one cycle of treatment at 99° C. for 4 seconds and at 66° C. for 30 seconds was repeated for 50 cycles, and fluorescence intensity of a reaction solution at 66° C. in each cycle was measured (wavelength of 515 nm to 545 nm) to obtain a threshold cycle (Ct value). From the results of the samples having the mt content of 100% using the mutant-type primer, theoretical values of the Ct values of respective samples were obtained.

The results thereof are shown in the following table 3. As can be seen from the following table 3, when the normal-type primer was used, although it was complementary to the normal-type, amplification was also detected in the sample having the mt content of 100%. Further, when the mutant-type primer was used, although it was complementary to the mutant-type, amplification was also observed in the sample having the wt content of 100%. From these results, it was found that the possibility of a false-positive is high in a conventional ASP-PCR method. Further, as a result of comparison with the theoretical values shown in the following table 3, since there are variations of about ±2 in actual measurement values, it is considered that the proportion of the mt content that can be detected appropriately is limited to mt 1% to mt 3%. These results showed that the method of Example 1 could achieve detection sensitivity superior to that of Comparative Example 2. Further, in the conventional ASP-PCR method of Comparative Example 2, reaction systems were required to be provided separately for detecting the normal-type and the mutant-type. However, according to Example 1, the normal-type and the mutant-type can be determined in one reaction system. Therefore, effort and cost for detecting a mutation can be reduced.

TABLE 3

| mt content of sample | Ct value (actual value) | | Ct theoretical value of mutant-type primer (Xmt) |
|---|---|---|---|
| | Normal-type primer (Xwt) | Mutant-type primer (Xmt) | |
| 100% | 36.1 | 26.6 | |
| 10% | 24.8 | 29.3 | 29.9 |
| 5% | 24.3 | 28.0 | 30.9 |
| 3% | 24.4 | 31.2 | 31.7 |
| 1% | 24.8 | 33.5 | 33.2 |
| 0.5% | 25.0 | 35.6 | 34.2 |
| 0.3% | 23.2 | 33.2 | 35.0 |
| 0.1% | 24.9 | 36.1 | 36.6 |
| 0% (wt 100%) | 24.7 | 32.9 | — |

Example 2

A point mutation (C→T) at the 944$^{th}$ base of the bcr-abl gene (sense strand) was detected by the Tm analysis according to the first embodiment of the present invention.

First, as a template for PCR, an oligonucleotide (antisense strand, SEQ ID NO: 6, hereinafter, referred to as "wt") complementary to a partial sequence of the normal-type bcr-abl gene that does not have a mutation at the 944$^{th}$ base C and an oligonucleotide (antisense strand, SEQ ID NO: 7, hereinafter, referred to as "mt") complementary to a partial sequence of the mutant-type bcr-abl gene in which the 944$^{th}$ base C is mutated into T were provided. It is to be noted that in the sequences of the normal-type oligonucleotide (wt) and the mutant-type oligonucleotide (mt), the bases written in capital letters respectively correspond to the 944$^{th}$ base of the normal-type bcr-abl gene and the 944$^{th}$ base of the mutant-type bcr-abl gene.

```
                                        SEQ ID NO: 6
Normal-type oligonucleotide (wt)
5'-gtaggtcatgaactcaGtgatgatatagaacgggggctcccgggtgc
aga-3'

SEQ ID NO: 7
Mutant-type oligonucleotide (mt)
5'-gtaggtcatgaactcaAtgatgatatagaacgggggctcccgggtgc
aga-3'
```

Both the oligonucleotides were mixed at predetermined proportions and thereby prepared plural nucleic acid samples. The mt contents in the plural nucleic acid samples were 100%, 3%, and 0%. In a tube, 1 μL of a 10 μmol/L nucleic acid reagent and 19 μL of the primer reagent shown in the following table 4 were added, and heated at 95° C. for 1 minute. After heating, 5 μL of the enzyme reagent shown in the following table 5 was further added to the tube, and PCR was conducted using a thermal cycler (product name: Mastercycler ep gradient S, produced by eppendorf). In PCR, one cycle of treatment at 95° C. for 5 seconds and at 62° C. for 15 seconds was repeated for 5 cycles. After PCR had completed, the tube was heated to 95° C., 2.5 μL of a 10% by weight SDS solution was added, and then the reaction was caused to be stopped. Further, the tube containing the PCR reaction solution was transferred to i-densy (product name, produced by ARKRAY, Inc.), treatments at 95° C. for 1 second and at 40° C. for 60 seconds were performed, and then the tube was heated from 40° C. to 75° C. with the temperature increasing at 1° C./3 sec rate. During this heating, the change in fluorescence intensity (excitation wavelength of 420 nm to 485 nm and detection wavelength of 520 nm to 555 nm) at each temperature from 40° C. to 60° C. was measured and the Tm analysis was conducted.

TABLE 4

| (Primer Reagent) | |
|---|---|
| dH$_2$O | 12.82 μL |
| buffer*$^1$ | 2 μL |
| 80% glycerol | 0.78 μL |
| 2.5 mmol/L dNTP | 2 μL |
| 5 μmol/L detection probe | 1 μL |
| 100 μmol/L normal-type primer (Xwt) | 0.2 μL |
| 100 μmol/L mutant-type primer (Xmt) | 0.2 μL |
| Total | 19 μL |

TABLE 5

| (Enzyme Reagent) | |
|---|---|
| dH$_2$O | 3.75 μL |
| buffer*$^1$ | 0.5 μL |
| 20 wt % BSA | 0.5 μL |
| 5 U/μL Gene Taq FP*$^2$ | 0.25 μL |
| Total | 5 μL |

The normal-type primer (Xwt) and the mutant-type primer (Xmt) are sense primers in PCR. The sequences of these primers are as follows. The normal-type primer (Xwt) is a sequence 100% identical to a region including the 944$^{th}$ base (C) in a sense strand of the normal-type bcr-abl gene, and the mutant-type primer (Xmt) is a sequence 100% identical to a region including the 944$^{th}$ base (T) in a sense strand of the mutant-type bcr-abl gene in which the 944$^{th}$ base C is mutated into T. It is to be noted that in the sequences of the normal-type primer (Xwt) and the mutant-type primer (Xmt), the bases at the 3' end written in capital letters respectively correspond to the 944$^{th}$ base of the normal-type bcr-abl gene and the 944$^{th}$ base of the mutant-type bcr-abl gene. The positional relationship among the normal-type primer (Xwt), the mutant-type primer (Xmt), and the antisense strand to which these primers are annealed can be seen in the schematic of FIG. 6. However, this is merely an exemplary scheme and does not limit the present invention.

```
                                        SEQ ID NO: 8
Normal-type primer (Xwt)
5'-ccccgttctatatcatcaC-3'

SEQ ID NO: 9
Mutant-type primer (Xmt)
5'-ggagccccgttctatatcatcaT-3'
```

As the detection probe, the same detection probe as that in Example 1 was used.

Figure 3:
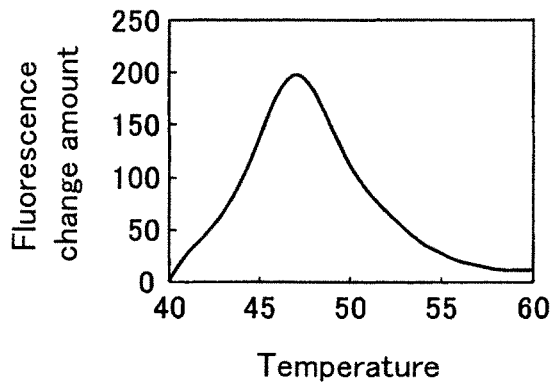
FIG. 3 includes graphs showing the results of Tm analysis in Example 2 of the present invention.
Figure 3:
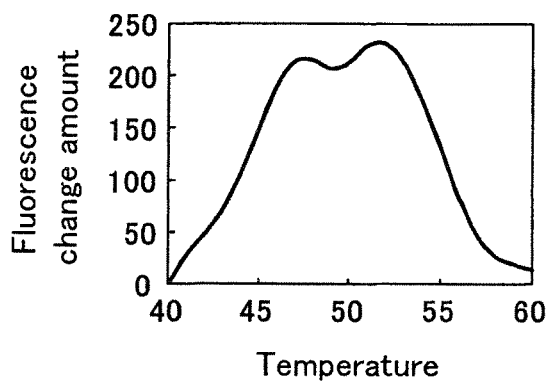
Figure 3:
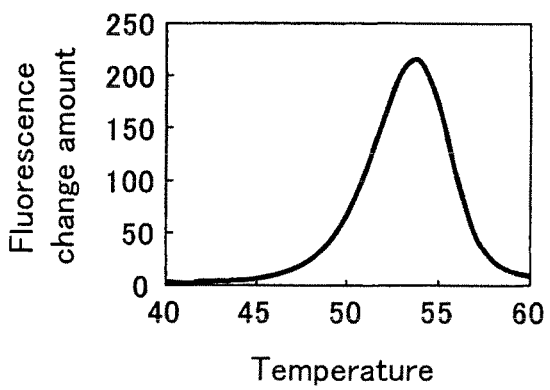

The results thereof are shown in FIG. 3. FIG. 3 shows graphs of the Tm analysis that show the change in fluorescence intensity accompanying the temperature rise. The horizontal axes indicate the temperature (° C.) at the time of measurement. The vertical axes indicate the change in fluorescence intensity (hereinafter, also referred to as "fluorescence change amount") and "d fluorescence intensity increase/dt" was used as the unit. As shown in FIG. 3, the peak of mt 100% (wt 0%), i.e., the Tm, was 52° C. to 54° C. and the peak of wt 100% (mt 0%), i.e., the Tm, was 47° C. to 48° C. With these as evaluation criteria of mt and wt, peaks of the Tm value of mt and the Tm value of wt with respect to respective samples were obtained. As a result, with respect to samples in which mt and wt are present (mt 3%), even though mt was 3%, which is very small amount, peaks of the Tm value of mt comparable to peaks of the Tm value of wt were observed.

Example 3

A point mutation (C→T) at the 944$^{th}$ base of the bcr-abl gene (sense strand) was detected by the Tm analysis according to the third embodiment of the present invention.

In the same manner as in Example 1, the normal-type plasmid (wt) and the mutant-type plasmid (wt) were mixed at predetermined proportions and thereby prepared plural nucleic acid samples. The mt contents in the plural nucleic acid samples were 100%, 10%, 5%, 3%, and 0%. In a tube, 1 μL (2×10$^4$ copies/test) of the nucleic acid sample and 24 μL of the PCR reaction solution shown in the following table 6 were added, and PCR was conducted using a thermal cycler (product name: Mastercycler ep gradient S, produced by eppendorf) in the same manner as in Example 1. The Tm analysis was conducted in the same manner as in Example 1 except that the change in fluorescence intensity (detection wavelength of 515 nm to 545 nm) at each temperature from 40° C. to 75° C. during 35 cycles after PCR was measured.

TABLE 6

(PCR reaction solution)

| | |
|---|---|
| H$_2$O | 16.94 μL |
| buffer*[1] | 2.5 μL |
| 80% glycerol | 1.56 μL |
| 2.5 mmol/L dNTP | 2 μL |
| 5 μmol/L detection probe | 0.25 μL |
| 100 μmol/L sense primer (Y2) | 0.125 μL |
| 100 μmol/L antisense primer (Y1) | 0.125 μL |
| 100 μmol/L mutant-type primer (Xmt) | 0.125 μL |
| 20 wt % BSA | 0.25 μL |
| 5 U/μL Gene Taq FP*[2] | 0.125 μL |
| Total | 24 μL |

The primer (Y2) is a sense primer in PCR and the primer (Y1) and the mutant-type primer (Xmt) are antisense primers in PCR. The same sense primer (Y2) and the mutant-type primer (Xmt) as those in Example 1 were used. The sequences of these primers are as follows. The mutant-type primer (Xmt) is a complementary sequence 100% matching with a region including the 944$^{th}$ base (T) in the mutant-type bcr-abl gene in which the 944$^{th}$ base C is mutated into T. It is to be noted that in the sequence of the mutant-type primer (Xmt), the base at the 3' end written in a capital letter corresponds to the 944$^{th}$ base of the mutant-type bcr-abl gene. The positional relationship between the sense primer (Y2) and the antisense strand to which this primer is annealed and the positional relationship among the normal-type primer (Xwt), the antisense primer (Y1), and the sense strand to which these primers are annealed can be seen in the schematic of FIG. 7. However, this is merely an exemplary scheme and does not limit the present invention.

SEQ ID NO: 1
Sense primer (Y2)
5'-ggacggacggaccgtcctcgttgtcttgttggc-3'

SEQ ID NO: 10
Antisense primer (Y1)
5'-gaccgaccgaccccaggaggttcccgtaggtc-3'

SEQ ID NO: 3
Mutant-type primer (Xmt)
5'-aggttcccgtaggtcatgaactcaA-3'

The sequence of the detection probe is shown as follows. The detection probe is a complementary sequence 100% matching with a region including the 944$^{th}$ base in an antisense strand of the mutant-type bcr-abl gene in which the 944$^{th}$ base C is mutated into T. In the following sequence, the base T written in a capital letter corresponds to the 944$^{th}$ mutated base A in the antisense strand. Further, P at the 3' end indicates a phosphate group.

SEQ ID NO: 11
Detection probe
5'-(BODIPY FL)-cccgttctatatcatcaTtgag-P-3'

Comparative Example 3

The Tin analysis was conducted in the same manner as in Example 3 except that, instead of 0.125 μL of the mutant-type primer (Xmt), a total of 0.25 μL of the antisense primer (Y1), which is a doubled amount, was added to the PCR reaction solution shown in the table 6.

Figure 4:
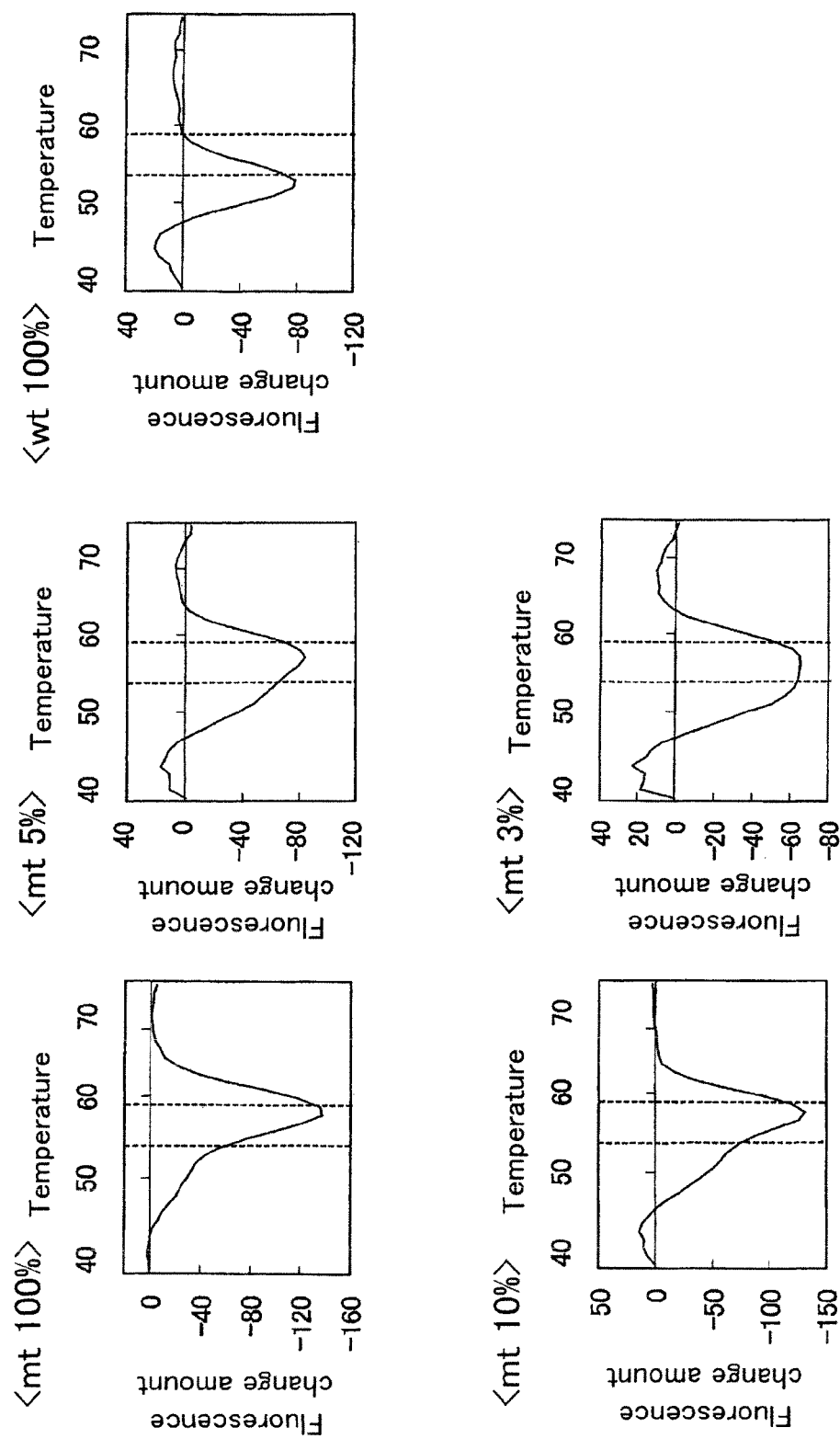
FIG. 4 includes graphs showing the results of Tm analysis in Example 3 of the present invention.
Figure 5:
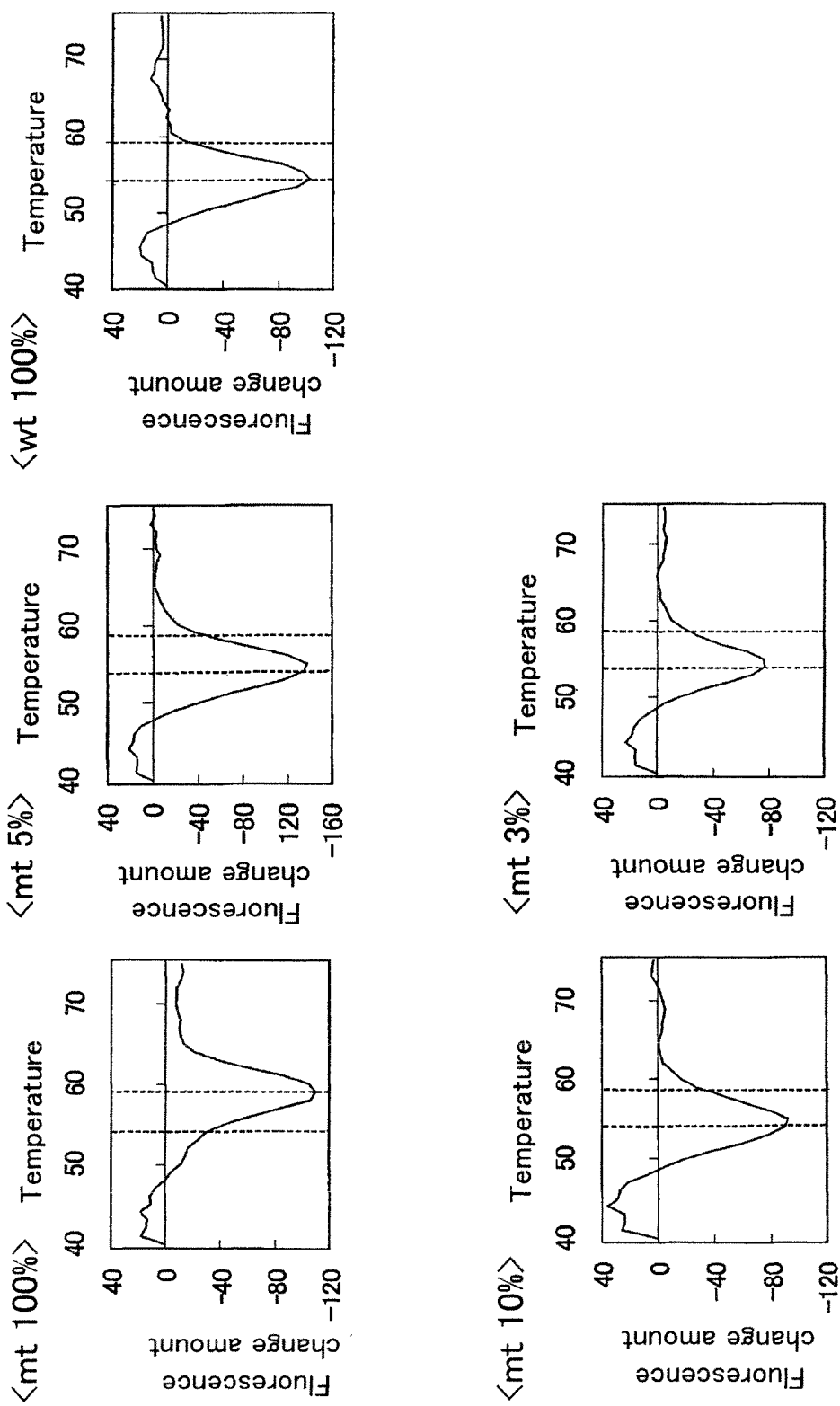
FIG. 5 includes graphs showing the results of Tm analysis in Comparative Example 3.

The results of Example 3 are shown in FIG. 4 and the results of Comparative Example 3 are shown in FIG. 5. FIGS. 4 and 5 show graphs of the Tin analysis that shows the change in fluorescence intensity accompanying the temperature rise. The horizontal axes indicate the temperature (° C.) at the time of measurement. The vertical axes indicate the change in fluorescence intensity (hereinafter, also referred to as "fluorescence change amount") and "–d fluorescence intensity increase/dt" was used as the unit. As can be seen from mt 100% (wt 0%) and wt 100% (mt 0%) in FIGS. 4 and 5, the peak of mt 100% (wt 0%), i.e., the Tm, was 59° C. and the peak of wt 100% (mt 0%), i.e., the Tm, was 54° C. With these as evaluation criteria of mt and wt, peaks of the Tm value of mt and the Tm value of wt with respect to respective samples were obtained. In Example 3 shown in FIG. 4, with respect to the samples in which mt and wt are present (mt. 3% to 10%), peaks of the Tm value of mt could be observed although the amount of not was small. In contrast, in Comparative Example 3 shown in FIG. 5, with respect to the samples in which mt and wt are present (mt 3% to 10%), peaks of the Tm value of wt were observed whereas peaks of the Tm value of mt were not observed. The results showed that a mutation can be detected with higher sensitivity according to this example.

INDUSTRIAL APPLICABILITY

As described above, according to the present invention, for example, even in a case where a template nucleic acid whose base site is a mutant-type and a template nucleic acid whose base site is a normal-type are present in a sample as template nucleic acids, the mutant-type target nucleic acid sequence is amplified preferentially over the normal-type target nucleic acid sequence. In this manner, by preferentially amplifying the mutant-type target nucleic acid sequence, for example, even in a case where the proportion of the mutant-type template nucleic acid is lower than that of the normal-type template nucleic acid, the presence or absence of the mutation can be detected with high sensitivity and high reliability by conducting the Tm analysis using a probe with reference to the amplification product of the present invention. Therefore, as described above, it is particularly useful for samples containing both normal genes and mutant genes. From these points, it can be said that the present invention is very useful, for example, in a clinical field in which treatment and diagnosis are conducted by detecting mutations of genes.

The invention claimed is:

1. A method of detecting a polymorphism at a polymorphism site in a target nucleic acid sequence, comprising
   (a) amplifying the target nucleic acid sequence comprising (i) a mutant-type target nucleic acid sequence comprising a mutant-type base at the polymorphism site or (ii) a normal-type target nucleic acid sequence comprising a normal-type base at the polymorphism site by using primer (Xmt) and primer (Xwt) in a same reaction system, wherein
   the primer (Xmt) is complementary to a region including the mutant-type target nucleic acid sequence and has a base complementary to the mutant-type base at a 3' region of the primer (Xmt),
   the primer (Xwt) is complementary to a region including the normal-type target nucleic acid sequence and has a base complementary to the normal-type base at a 3' region of the primer (Xwt),
   the length of the primer (Xmt) is 1 to 5 bases longer than the length of the primer (Xwt), and
   the amplification efficiency by the primer (Xmt) is higher than the amplification efficiency by the primer (Xwt),
   (b) changing a temperature of the reaction system containing an amplification product obtained in the step (a) in the presence of a probe which hybridizes to a sequence including the polymorphism site, and measuring a signal value that shows a molten state of a hybridization product between the amplification product and the probe; and
   (c) determining the presence or absence of mutation of the objective polymorphism site from a change in the signal value accompanying a change in the temperature.

2. The method according to claim 1, wherein the primer (Xmt) and the primer (Xwt), a first or a second base at a 3' end is a base complementary to a base of the polymorphism site.

3. The method according to claim 1, wherein a Tm value of the primer (Xmt) with reference to a complementary sequence is higher than a Tm value of the primer (Xwt) with reference to a complementary sequence.

4. The method according to claim 1, wherein the same reaction system of the amplification step contains primer (Y1), wherein:
the primer (Y1) is complementary to a region at a 3' side relative to the polymorphism site in the target nucleic acid sequences.

5. The method according to claim 4, wherein the same reaction system of the amplification step contains primer (Y2), wherein:
the primer (Y2) is complementary to a complementary sequence for a region at a 5' side relative to the polymorphism site in the target nucleic acid sequences.

6. The method according to claim 1, where in the amplification step, a probe which hybridizes to a sequence including the polymorphism site is further added to the reaction system.

7. The method according to claim 6, wherein the probe is a labeled probe.

8. The method according to claim 1, wherein the step (a), in advance of an amplification of the target nucleic acid sequence, a probe which hybridizes to a sequence including the polymorphism site in the target nucleic acid sequence is further added to the reaction system.

9. The method according to claim 8, wherein the probe is a labeled probe.

10. The method according to claim 9, wherein the labeled probe is a labeled probe that exhibits a signal independently but does not exhibit a signal by hybridization, or a labeled probe that does not exhibit a signal independently but exhibits a signal by hybridization.

11. The method according to claim 1, wherein the length of the primer (Xmt) is longer than the length of the primer (Xwt).

12. The method according to claim 1, wherein the guanine-cytosine content of the primer (Xmt) is higher than that of the primer (Xwt).

13. The method according to claim 1, wherein the polymorphism site in a target nucleic acid sequence is in a bcr-abl gene at the 944th base of the bcr-abl gene.

14. The method according to claim 1, wherein the primer (Xmt) comprises a base sequence of SEQ ID NO: 3, and the primer (Xwt) comprises a base sequence of SEQ ID NO: 2.

15. The method according to claim 14, wherein the probe comprises a base sequence of SEQ ID NO: 4.

16. The method according to claim 1, wherein the primer (Xmt) comprises a base sequence of SEQ ID NO: 9, and the primer (Xwt) comprises a base sequence of SEQ ID NO: 8.

17. The method according to claim 16, wherein the probe comprises a base sequence of SEQ ID NO: 11.

18. The method according to claim 1, wherein
the primer (Xmt) comprises a base sequence of SEQ ID NO: 3 or 9;
the primer (Xwt) comprises a base sequence of SEQ ID NO: 2 or 8; and
the probe comprises a base sequence of SEQ ID NO: 4 or 11.

* * * * *

SEQUENCE LISTING

<160> NUMBER OF SEQ ID NOS: 11

<210> SEQ ID NO 1
<211> LENGTH: 33
<212> TYPE: DNA
<213> ORGANISM: Artificial
<220> FEATURE:
<223> OTHER INFORMATION: synthetic primer

<400> SEQUENCE: 1
ggacggacgg accgtcctcg ttgtcttgtt ggc                      33

<210> SEQ ID NO 2
<211> LENGTH: 22
<212> TYPE: DNA
<213> ORGANISM: Artificial
<220> FEATURE:
<223> OTHER INFORMATION: synthetic primer

<400> SEQUENCE: 2
ttcccgtagg tcatgaactc ag                                  22

<210> SEQ ID NO 3
<211> LENGTH: 25
<212> TYPE: DNA
<213> ORGANISM: Artificial
<220> FEATURE:
<223> OTHER INFORMATION: synthetic primer

<400> SEQUENCE: 3
aggttcccgt aggtcatgaa ctcaa                               25

<210> SEQ ID NO 4
<211> LENGTH: 20
<212> TYPE: DNA
<213> ORGANISM: Artificial
<220> FEATURE:
<223> OTHER INFORMATION: synthetic probe

<400> SEQUENCE: 4
ctcaatgatg atatagaacg                                     20

<210> SEQ ID NO 5
<211> LENGTH: 34
<212> TYPE: DNA
<213> ORGANISM: Artificial
<220> FEATURE:
<223> OTHER INFORMATION: synthetic primer

<400> SEQUENCE: 5
ggacggacgg accgcactcc ctcaggtagt ccag                     34

<210> SEQ ID NO 6
<211> LENGTH: 50
<212> TYPE: DNA
<213> ORGANISM: Artificial
<220> FEATURE:
<223> OTHER INFORMATION: synthetic sequence

<400> SEQUENCE: 6
gtaggtcatg aactcagtga tgatatagaa cggggggctcc cgggtgcaga   50

<210> SEQ ID NO 7
<211> LENGTH: 50
<212> TYPE: DNA
<213> ORGANISM: Artificial

```
<220> FEATURE:
<223> OTHER INFORMATION: synthetic sequence

<400> SEQUENCE: 7
gtaggtcatg aactcaatga tgatatagaa cgggggctcc cgggtgcaga        50

<210> SEQ ID NO 8
<211> LENGTH: 20
<212> TYPE: DNA
<213> ORGANISM: Artificial
<220> FEATURE:
<223> OTHER INFORMATION: synthetic primer

<400> SEQUENCE: 8
cccccgttct atatcatcac                                         20

<210> SEQ ID NO 9
<211> LENGTH: 24
<212> TYPE: DNA
<213> ORGANISM: Artificial
<220> FEATURE:
<223> OTHER INFORMATION: synthetic primer

<400> SEQUENCE: 9
ggagcccccg ttctatatca tcat                                    24

<210> SEQ ID NO 10
<211> LENGTH: 32
<212> TYPE: DNA
<213> ORGANISM: Artificial
<220> FEATURE:
<223> OTHER INFORMATION: synthetic primer

<400> SEQUENCE: 10
gaccgaccga ccccaggagg ttcccgtagg tc                           32

<210> SEQ ID NO 11
<211> LENGTH: 22
<212> TYPE: DNA
<213> ORGANISM: Artificial
<220> FEATURE:
<223> OTHER INFORMATION: synthetic probe

<400> SEQUENCE: 11
cccgttctat atcatcattg ag                                      22
```